US012780836B2

(12) United States Patent
Gu et al.

(10) Patent No.: US 12,780,836 B2
(45) Date of Patent: Nov. 3, 2026

(54) PREPARATION AND APPLICATION OF TRICYCLIC PYRIMIDINONE COMPOUND AND ITS COMPOSITION

(71) Applicant: SHANGHAI DEEP POTENTIAL TECHNOLOGY CO., LTD., Shanghai (CN)

(72) Inventors: Zhenghua Gu, Shanghai (CN); Dongqin Wang, Shanghai (CN); Youhong Hu, Shanghai (CN)

(73) Assignee: SHANGHAI DEEP POTENTIAL TECHNOLOGY CO., LTD., Shanghai (CN)

( * ) Notice: Subject to any disclaimer, the term of this patent is extended or adjusted under 35 U.S.C. 154(b) by 569 days.

(21) Appl. No.: 18/003,989

(22) PCT Filed: Jun. 25, 2021

(86) PCT No.: PCT/CN2021/102420
§ 371 (c)(1),
(2) Date: Dec. 30, 2022

(87) PCT Pub. No.: WO2022/001881
PCT Pub. Date: Jan. 6, 2022

(65) Prior Publication Data

US 2023/0271980 A1 Aug. 31, 2023

(30) Foreign Application Priority Data

Jun. 30, 2020 (CN) ......................... 202010608551.1
Sep. 11, 2020 (CN) ......................... 202010952714.8

(51) Int. Cl.

| | |
|---|---|
| ***C07D 487/16*** | (2006.01) |
| ***A61K 31/519*** | (2006.01) |
| ***A61K 31/5383*** | (2006.01) |
| ***A61K 31/542*** | (2006.01) |
| ***A61K 31/551*** | (2006.01) |
| ***A61K 31/553*** | (2006.01) |
| ***A61K 31/554*** | (2006.01) |
| ***A61P 3/10*** | (2006.01) |
| ***A61P 7/10*** | (2006.01) |
| ***A61P 9/00*** | (2006.01) |
| ***A61P 9/10*** | (2006.01) |
| ***A61P 13/08*** | (2006.01) |
| ***A61P 25/00*** | (2006.01) |
| ***A61P 25/28*** | (2006.01) |
| ***A61P 27/02*** | (2006.01) |
| ***A61P 27/06*** | (2006.01) |
| ***C07D 498/16*** | (2006.01) |
| ***C07D 513/16*** | (2006.01) |

(52) U.S. Cl.
CPC ................................ *C07D 498/16* (2013.01)

(58) Field of Classification Search
CPC .. C07D 487/16; C07D 498/16; C07D 513/16; A61K 31/519; A61K 31/5383; A61K 31/542; A61K 31/551; A61K 31/553; A61K 31/554; A61P 3/10; A61P 7/10; A61P 9/00; A61P 9/10; A61P 13/08; A61P 25/00; A61P 25/28; A61P 27/02; A61P 27/06
See application file for complete search history.

(56) References Cited

FOREIGN PATENT DOCUMENTS

| | | |
|---|---|---|
| WO | 2013013503 A1 | 1/2013 |
| WO | 2014114694 A1 | 7/2014 |
| WO | 2016011931 A1 | 1/2016 |
| WO | 2016012916 A1 | 1/2016 |

OTHER PUBLICATIONS

International Search Report and Written Opinion issued is International Application No. PCT/CN2021/102420; mailed Sep. 27, 2021; 15 pgs.
First Office Action issued in Chinese Application No. 202010952714.8; mailed Jun. 8, 2022; 13 pgs.
Bertilsson et al., “Changes in Gene Transcription Underlying the Aberrant Citrate and Choline Metabolism in Human Prostate Cancer Samples”, Clinical Cancer Research, Jun. 15, 2012; 9 pgs.
Buschini et al., “Age related macular degeneration and drusen: Neuroinflammation in the retina”, Progress in Neurobiology 95 (2011) 14-25; 12 pgs.
Examination Report in Corresponding Australian Application No. 2021301865, dated Jun. 21, 2023; 3 pgs.
Extended Search Report in Corresponding European Application No. 21834246.7, mailed Jul. 2, 2024; 5 pgs.
Fitzpatrick AL, Irizarry MC, Cushman M, Jenny NS, Chi GC, Koro C, “Lipoprotein-associated phospholipase A2 and Risk of Dementia in the Cardiovascular Health Study”, Atherosclerosis (2014), doi: 10.1016/j.atherosclerosis.2014.04.032; 31 pgs.
Gareth Maher-Edwards et al., “A 24-week study to evaluate the effect of rilapladib on cognition and cerebrospinal fluid biomarkers of Alzheimer’s disease”, Alzheimer’s & Dementia: Translational Research & Clinical Interventions 1 (2015) 131-140; 10 pgs.
Invitation to Respond to Written Opinion in Corresponding Singapore Application No. 11202261723V, dated Jan. 15, 2025; 10 pgs.
Notice of Reasons for Rejection in Corresponding Japanese Application No. 2022-580770, dated Mar. 4, 2024; 7 pgs.
Official Action of the Substantive Examination in Corresponding Russian Application No. 2022135421/04, dated Nov. 17, 2023; 27 pgs.
Request for the Submission of an Opinion in Corresponding Korean Application No. 10-2023-7003346, dated May 13, 2025; 12 pgs.
Staurenghi et al., “Darapladib, a Lipoprotein-Associated Phospholipase A2 Inhibitor, in Diabetic Macular Edema”, American Academy of Ophthalmology, 2015; 7 pgs.

*Primary Examiner* — Brenda L Coleman
(74) *Attorney, Agent, or Firm* — HAUPTMAN HAM, LLP

(57) ABSTRACT

Disclosed is a tricyclic pyrimidinone compound of Formula (I) or a pharmaceutically acceptable salt thereof, which is an entirely new Lp-PLA2 inhibitor useful in treating neurodegeneration-related diseases such as Alzheimer’s disease (AD), glaucoma and age-related macular degeneration (AMD), or cardiovascular diseases including atherosclerosis.

13 Claims, No Drawings

PREPARATION AND APPLICATION OF TRICYCLIC PYRIMIDINONE COMPOUND AND ITS COMPOSITION

RELATED APPLICATIONS

The present application is a U.S. National Phase of International Application Number PCT/CN2021/102420, filed Jun. 25, 2021, and claims priority to Chinese Application Number 202010608551.1, filed Jun. 30, 2020, and Chinese Application Number 202010952714.8, filed Sep. 11, 2020.

TECHNICAL FIELD

The invention belongs to the field of medicine, and in particular relates to a tricyclic pyrimidinone compound, its preparation method, its medicinal composition, and its use in medicine.

BACKGROUND

Lipoprotein-associated phospholipase A2 (Lp-PLA2) is a member of the phospholipase A2 superfamily (Dennis E A, Cao J, Hsu Y H, Magrioti V, Kokotos G. *Chem Rev.* 2011, 111, 6130-6185). It is mainly secreted by monocytes, macrophages, T lymphocytes and chief cells (Stafforini D M, Elstad M R, McIntyre T M, Zimmerman G A, Prescott S M. J Biol Chem. 1990, 265: 9682-9687; Nakajima K, Murakami M, Yanoshita R, Samejima Y, Karasawa K, Setaka M, Nojima S Kudo I. J Biol Chem. 1997, 272, 19708-19713). Phosphatidylcholine sn-2 esters are produced during the oxidation of low-density lipoprotein (LDL). Lp-PLA2 is responsible for the hydrolysis of oxidized phosphatidylcholine sn-2 ester, which then produces oxidized fatty acids and lysophosphatidylcholine (LysoPC) (Caslake M J, Packard C J, Suckling K E, Holmes S D, Chamberlain P, Macphee C H. Atherosclerosis. 2000, 150, 413-419; MacPhee C H, Moores K E, Boyd H F, Dhanak D, Ife R J, Leach C A, Leake D S, Milliner K J, Patterson R A, Suckling K E, Tew D G, Hickey D M. Biochem J. 1999, 338, 479-487). Both oxidized fatty acids and LysoPC play roles in activating macrophages, increasing oxidative stress, affecting the function of T lymphocytes, and inducing inflammatory responses (Quinn M T, Parthasarathy S, Steinberg D. Proc Natl Acad Sci USA. 1988, 85, 2805-2809). LysoPCs have been reported to induce the release of multiple cytotoxic inflammatory cytokines (Shi, et al, Atherosclerosis, 2007, 191, 54-62). In addition, LysoPCs have also been involved in the activation of leukocytes, the induction of apoptosis, and the mediation of endothelial dysfunction (Wilensky et al, Current Opinion in Lipidology, 2009, 20, 415-420).

It has been reported that plasma level of Lp-PLA2 is associated with cardiovascular diseases (Fitzpatrick A L, Irizarry M C, Cushman M, Jenny N S, Chi G C, Koro C. *Atherosclerosis.* 2014, 235, 384-391), diabetic macular edema (DME) (Staurenghi G, Ye L, Magee M H, Danis R P, Wurzelmann J, Adamson P, McLaughlin M M, Darapladib DMES G. *Ophthalmology.* 2015, 122, 990-996), and prostate cancer (Bertilsson H, Tessem M B, Flatberg A, Viset T, Gribbestad I, Angelsen A, Halgunset J. *Clin Cancer Res.* 2012, 18, 3261-3269).

Alzheimer's disease (AD) is a chronic neurodegenerative disease that results in decreased cognitive abilities, mood swings, irreversible memory loss, disorientation, speech impairment, and loss of self-protection (Hardy J, et al. Science 2002, 297, 353-356). Alzheimer's disease usually starts slowly and gets worse over time, which is the cause of 60% to 70% of dementia cases and affects about 6% of the population over 65 years old. AD patients will gradually withdraw from family and society, rely more and more on help, and eventually progress to death. AD is one of the most costly diseases in developed countries and also with high costs in other countries. These costs will increase dramatically, especially as aging becomes a major societal issue. Needless to say, AD is a complex disease involving multiple factors. Although the etiology of AD has not been fully elucidated, it is clear that several factors are involved in the initiation and progression of the disease, including aggregated tau protein and Aβ peptide, oxidative stress, and neuroinflammation (Echeverria V, Yarkov A, Aliev G. *Prog Neurobiol.* 2016, 144, 142-157). The current research and development of AD drug is maily focused on targets of Aβ amyloidosis and tau (Chiang K, Koo E H. *Annu Rev Pharmacol Toxicol.* 2014, 54, 381-405; Awasthi M, Singh S, Pandey V P, Dwivedi U N. *J Neurol Sci.* 2016, 361, 256-271). However, despite strong preclinical data, results from late-stage clinical trials have so far failed to demonstrate clinical efficacy. These disappointing results suggest that other mechanisms of neuropathology, such as oxidative stress and neuroinflammation, may have to be explored for AD therapy.

Elevated levels of Lp-PLA2 in plasma increase the risk of dementia, including AD (Van Oijen, et al. Annals of Neurology, 2006, 59, 139). In addition to vascular dementia and mixed dementia, high oxidized LDL levels have been found in AD patients (Maher-Edwards G, De'Ath J, Barnett C, Lavrov A, Lockhart A, Alzheimer's & Dementia: Translational Research & Clinical Interventions. 2015, 1, 131-140; Kassner et al. Current Alzheimer Research, 2008, 5, 358-366; Dildar, et al., Alzheimer Dis Assoc Disord, 24, Apr.-Jun. (2010); Sinem, et al. Current Alzheimer Research, 2010, 7, 463-469). Neuroinflammation and upregulation of multiple inflammatory cytokines were also found in AD patients (Colangelo, et al., Journal of Neuroscience Research, 2002, 70, 462-473; Wyss-Coray, Nature Medicine, 2006, 12, Sep.).

Based on all these findings, Lp-PLA2 is a potential target for the treatment of AD, and this is further confirmed by the clinical results of the Lp-PLA2 inhibitor Rilapladib for AD patients (Maher-Edwards G, De'Ath J, Barnett C, Lavrov A, Lockhart A, *Alzheimer's & Dementia: Translational Research & Clinical Interventions.* 2015, 1, 131-140).

Glaucoma and age-related macular degeneration (AMD) are retinal neurodegenerative diseases. Buschini et al reported that inflammation, including TNF-α signaling, may play an important role in the pathogenesis of glaucoma and AMD (Buschini et al, Progress in Neurobiology, 2011, 95, 14-25; Tezel, Progress in Brain Research, vol. 173, ISSN0079-6123, Chapter 28). Additionally, Shi et al demonstrated that Lp-PLA2 inhibitors can block the release of inflammatory cytokines (Shi, et al, Atherosclerosis, 2007, 191, 54-62). Inhibition of Lp-PLA2 is potential treatment for glaucoma and AMD.

A number of Lp-PLA2 inhibitors have been reported, including β-lactams (Tew D G, Boyd H F, Ashman S, Theobald C, Leach C A. Biochemistry. 1998, 37, 10087-10093), oximes (Jeong T S, Kim M J, Yu H, Kim H S, Choi J K, Kim S S, Lee W S. Bioorg Med Chem Lett. 2005, 15, 1525-1527; Jeong H J, Park Y D, Park H Y, Jeong I Y, Jeong T S, Lee W S. Bioorg Med Chem Lett. 2006, 16, 5576-5579), amides of xanthuric acid (Lin E C, Hu Y, Amantea C M, Pham L M, Cajica J, Okerberg E, Brown H E, Fraser A, Du L, Kohno Y, Ishiyama J, Kozarich J W, Shreder K R. Bioorg Med Chem Lett. 2012, 22, 868-871; Hu Y, Lin E C, Pham L M, Cajica J, Amantea C M, Okerberg E, Brown H E, Fraser A, Du L, Kohno Y, Ishiyama J, Kozarich J W, Shreder K R. Bioorg Med Chem Lett. 2013, 23, 1553-1556), and carbamates (Nagano J M, Hsu K L, Whitby L R, Niphakis M J, Speers A E, Brown S J, Spicer T, Fernandez-Vega V, Ferguson J, Hodder P, Srinivasan P, Gonzalez T D, Rosen H, Bahnson B J, Cravatt B F. Bioorg Med Chem Lett. 2013, 23, 839-843).

The Lp-PLA2 inhibitor Darapladib has been reported as a potential therapy against atherosclerosis and DME (Magrioti V, Kokotos G. *Expert Opin Ther Pat.* 2013; 23: 333-344).

SUMMARY

The present inventors have found that Lp-PLA2 inhibitors play an important role in the treatment of neurodegenerative related diseases, such as Alzheimer's disease (AD), glaucoma and age-related macular degeneration (AMD), or cardiovascular diseases including atherosclerosis. For this reason, the present inventors have developed a novel type of Lp-PLA2 inhibitor, tricyclic pyrimidinone compound The tricyclic pyrimidinone compound is a compound having a structure represented by Formula (I) or a pharmaceutically acceptable salt thereof, (I)

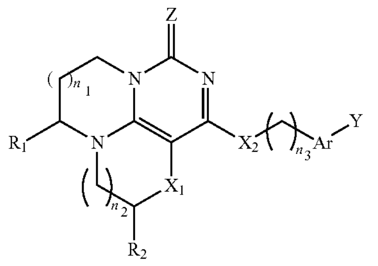

wherein

- $n_1$, $n_2$, and $n_3$ are each independently 0, 1, or 2;
- $R_1$ and $R_2$ are each independently selected from —H, hydroxyl, cyano, halogen, alkyl, deuterated alkyl, hydroxyalkyl, haloalkyl, cycloalkyl, alkoxy, haloalkoxy, deuterated alkoxy;
- $X_1$ and $X_2$ are each independently selected from alkylene, —O—, —S—, or —NR'—,
- R' is selected from —H, alkyl, deuterated alkyl, or cycloalkyl;
- Ar is an arylene group or a heteroarylene group, wherein hydrogen atoms in the arylene or heteroarylene are optionally substituted by 0, 1 or more substituents, and the substituents are each independently selected from halogen, alkyl, deuteroalkyl, haloalkyl, alkoxy, deuteroalkoxy, haloalkoxy, hydroxy, hydroxyalkyl, cyano, amino, monoalkyl- or dialkyl-substituted amino, nitro, carboxyl, aldehyde, cycloalkyl, heterocyclyl, aryl, or heteroaryl;
- Y is —H, halogen, alkyl, haloalkyl, haloalkoxy, cycloalkyl, alkoxy, deuterated alkyl, deuterated alkoxy, —OAr', —SAr', —NH—Ar', —NMe—Ar', —NR'', or —R'''—Ar;
- Ar' is selected from aryl or heteroaryl, wherein hydrogen atoms in the aryl or heteroaryl are optionally substituted with one or more substituents, the substituents are each independently selected from halogen, alkyl, deuterated alkyl, haloalkyl, alkoxy, deuterated alkoxy, hydroxy, hydroxyalkyl, haloalkoxy, cyano, amino, nitro, carboxyl, aldehyde, cycloalkyl, heterocyclyl, aryl, or heteroaryl;
- R" is alkyl;
- R" is alkylene;
- Z is O or S.

Optionally, halogens in the "halogen" "haloalkyl" and "haloalkoxy" are each independently selected from F, Cl, Br, or I;

- optionally, alkyls in the "alkyl" "deuterated alkyl" "hydroxyalkyl" "haloalkyl" "haloalkoxy", "alkoxy" and "mono- or di-alkyl substituted amino" are each independently $C_1$-$C_{10}$ linear or branched alkyl; optionally each independently $C_1$-$C_7$ linear or branched alkyl;
- optionally each independently $C_1$-$C_4$ linear or branched alkyl; and optionally selected from methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl;
- optionally, "alkylenes" are each independently $C_1$-$C_{10}$ linear or branched alkylene;
- optionally each $C_1$-$C_7$ linear or branched alkylene; optionally each $C_1$-$C_5$ linear or branched alkylene; and optionally each selected from methylene, ethylene, n-propylene, iso-propylene, n-butylene, iso-butylene, tert-butylene, sec-butylene, n-pentylene, 1-methylbutylene, 2-methylbutylene, 3-methylbutylene, isopentylene, 1-ethylpropylene, neopentylene, n-hexylene, 1-methylpentylene, 2-methylpentylene, 3-methylpentylene, isohexylene, 1,1-dimethylbutylene, 2,2-dimethylbutylene, 3,3-dimethylbutylene, 1,2-dimethylbutylene, 1,3-dimethylbutylene, 2,3-dimethylbutylene, 2-ethylbutylene, n-heptylene, 2-methylhexylene, 3-methylhexylene, 2,2-dimethylpentylene, 3,3-dimethylpentylene, 2,3-dimethylpentylene, 2,4-dimethylpentylene, 3-ethylpentylene, or 2,2,3-trimethylbutylene;
- optionally, "cycloalkyl" is $C_3$-$C_{10}$ monocyclic or bicyclic cycloalkyl, optionally $C_3$-$C_7$ monocyclic cycloalkyl, and optionally cyclopropyl, cyclobutyl, cyclopentyl, cyclohexyl, or cycloheptyl;
- optionally, "heterocyclyl" is 3- to 10-membered non-aromatic heterocycle ring containing 1, 2, or 3 heteroatoms selected from N, O, and S; optionally 3- to 10-membered non-aromatic ring containing 1 or 2 heteroatoms selected from N and O; optionally 3- to 6-membered non-aromatic ring containing 1 or 2 heteroatoms selected from N and O;
- optionally 3- to 10-membered non-aromatic ring containing 1 or 2 heteroatoms selected from N and S; and optionally 3- to 6-membered non-aromatic ring containing 1 or 2 heteroatoms selected from N and S;
- optionally, "aryl" is 6- to 10-membered aryl; optionally phenyl or naphthyl, and optionally phenyl, 1-naphthyl, or 2-naphthyl;
- optionally, "arylene" is 6- to 10-membered arylene; and optionally phenylene or naphthylene;
- optionally, "heteroaryl" is 5- to 10-membered heteroaryl ring containing 1-3 heteroatoms selected from N, O, and S; optionally 5- to 10-membered heteroaryl ring containing 1-2 heteroatoms selected from N, O, and S; optionally the heteroaryl ring is selected from pyridine ring, pyrrole ring, pyrazole ring, pyrimidine ring, pyrazine ring, pyridazine ring, thiophene ring, and furan ring; optionally selected from pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, pyrazin-3-yl, indolyl, isoindolyl, indazolyl, indolizinyl, purinyl, quinolizinyl, quinolinyl, isoquinolinyl, cinnolinyl, phthalazinyl, naphthyridinyl, quinazolinyl, quinoxalinyl, thieno[2,3-b]furanyl, furo[3,2-b]-pyranyl, pyrido[2,3-d]oxazinyl, pyrazolo[4,3-d]oxazolyl, imidazo[4,5-d]thiazolyl, pyrazino[2,3-d]pyridazinyl, imidazo[2,1-b]thiazolyl, imidazo[1,2-b][1,2,4]triazinyl, benzothienyl, benzoxazolyl, benzimidazolyl, benzothiazolyl, benzoxepinyl, benzoxazinyl, benzofuranyl, benzotriazolyl, pyrrolo[2,3-b]pyridyl, pyrrolo[3,2-c]pyridinyl, pyrrolo[3,2-b]pyridyl, imidazo[4,5-b]pyridyl, imidazo[4,5-c]pyridyl, pyrazolo[4,3-d]pyridyl, pyrazolo[4,3-c]pyridyl, pyrazolo[3,4-c]pyridinyl, pyrazolo[3,4-d]pyridyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazolo[2,3-b]pyrazinyl, or pyrimido[4,5-d]pyrimidinyl; and is optionally selected from pyridin-2-yl, pyridin-3-yl, pyridin-4-yl, pyrimidin-2-yl, pyrimidin-4-yl, or pyrimidin-5-yl;

optionally, "heteroarylene" is 5- to 10-membered heteroarylene ring containing 1-3 heteroatoms selected from N, O, and S; optionally 5- to 10-membered heteroaromatic ring containing 1-2 heteroatoms selected from N, O, and S; and optionally the heteroarylene ring is selected from pyridine ring, pyrrole ring, pyrazole ring, pyrimidine ring, pyrazine ring, pyridazine ring, thiophene ring, furan ring Optionally, $n_1$, $n_2$, and $n_3$ are each independently 0, 1, or 2.

Optionally, $n_1$ is 0 or 1.

Optionally, $n_1$ is 0.

Optionally, $n_2$ is 0 or 1.

Optionally, $n_2$ is 1.

Optionally, $n_3$ is 1.

Optionally, $R_1$ and $R_2$ are each independently selected from —H, fluorine, chlorine, bromine, hydroxyl, cyano, $C_1$-$C_7$ alkyl (such as methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), $C_1$-$C_3$ deuteroalkyl (such as —$CD_3$, —$C_2D_5$, or —$C_3D_7$), $C_1$-$C_3$ deuteroalkoxyl (such as —$OCD_3$, —$OC_2D_5$, or —$OC_3D_7$), haloalkyl, haloalkoxyl, cyclopropanyl, cyclobutanyl, cyclopentanyl; optionally, $R_1$ is —H or —$CH_3$; and optionally, $R_1$ is —H, $R_2$ is —H;

optionally, $X_1$ and $X_2$ are each independently selected from $C_1$-$C_7$ alkylene (optionally, —$CH_2$—, ethylene, n-propylene, isopropylene, n-butylene, or isobutylene), —O—, —S—, or —NR—;

optionally, $X_1$ is —$CH_2$—, or —O—; optionally, $X_1$ is —O—; optionally, $X_2$ is —O—;

optionally, R' is selected from —H, $C_1$-$C_7$ alkyl (optionally, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), deuterated alkyl (optionally, —$CD_3$, —$C_2D_5$, or —$C_3D_7$), or $C_3$-$C_6$ cycloalkyl (optionally, cyclopropanyl, cyclobutanyl, cyclopentanyl, or cyclohexanyl);

optionally, Ar is phenylene or pyridyl, wherein hydrogen atoms in the phenylene or pyridyl are optionally substituted with 0, 1, 2, or 3 substituents, the substituents are each independently selected from F, Cl, Br, I, —CN, -Me, —$C_2H_5$, cyclopropyl, —$CD_3$, —OMe, —$OCD_3$, —$CF_3$, or —$OCF_3$; optionally, Ar is phenylene, wherein the hydrogen atom in the phenylene is optionally substituted by 2 substituents, and the substituent is F;

optionally, Y is —H, —F, —Cl, —Br, methyl, ethyl, n-propyl, isopropyl, —$CD_3$, —$CF_3$, —$CH_2CF_3$, —$OCHF_2$, —$OCH_2F$, cyclopropyl, cyclobutyl, cyclopentyl, —$OCH_3$, —$OCD_3$, —$OC_2H_5$, —$OC_3H_7$, or —OAr';

optionally, Y is H, halogen, or —OAr'; and optionally, Y is H, —F, or —OAr';

Ar' is selected from phenyl, pyridyl, pyrimidyl, pyrrolyl, pyrazolyl, thienyl or quinolinyl, and the phenyl, pyridyl, pyrimidyl, pyrrolyl, pyrazolyl, thienyl or quinoline optionally, Ar' is selected from phenyl, pyridyl, pyrimidyl, pyrrolyl, pyrazolyl, thienyl or quinolinyl, wherein hydrogen atoms in the phenyl, pyridyl, pyrimidyl, pyrrolyl, pyrazolyl, thienyl or quinolinyl ring are each independently optionally substituted with 1, 2, or 3 sub stituents, the sub stituents are each independently selected from F, Cl, Br, —CN, $C_1$-$C_7$ alkyl (optionally, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), —$CD_3$, $C_1$-$C_6$ haloalkyl, —$OCH_3$, —$OCD_3$, —$OC_2H_7$, —$OC_3H_7$, $C_1$-$C_6$ haloalkoxyl, or $C_3$-$C_6$ cycloalkyl (optionally, cyclopropanyl, cyclobutanyl, cyclopentanyl, or cyclohexanyl);

optionally, Ar' is selected from phenyl, pyridin-3-yl, pyridin-4-yl, or pyrimidin-5-yl, and is optionally substituted with 1 or 2 substituents, the substituents are selected from F, Cl, —$CH_3$, —$CF_3$, or —$OCF_3$;

optionally, Z is O.

Optionally, of a compound of Formula (I) or a pharmaceutically acceptable salt thereof, the compound of Formula (I) is selected from the following compounds:

1
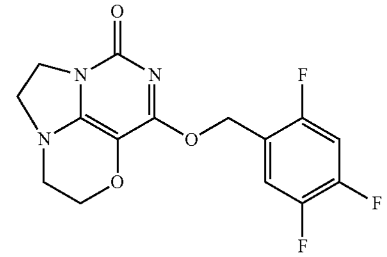
2
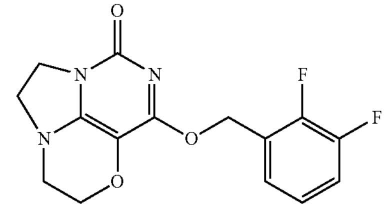
3
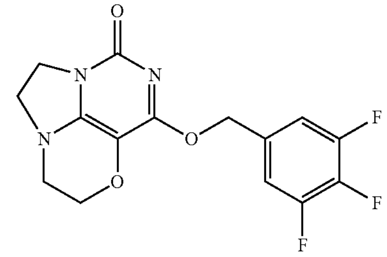
4
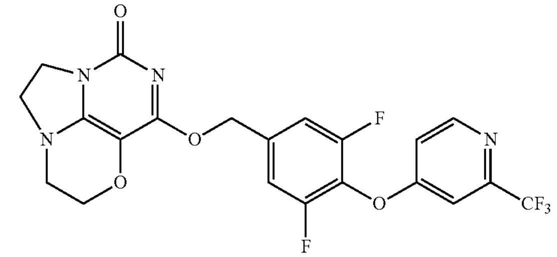
5
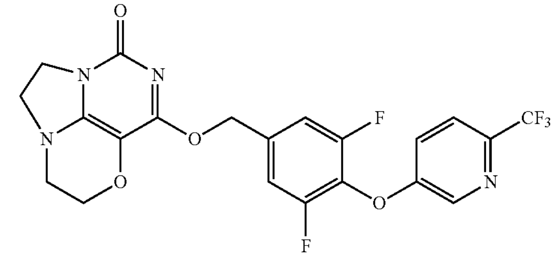
6
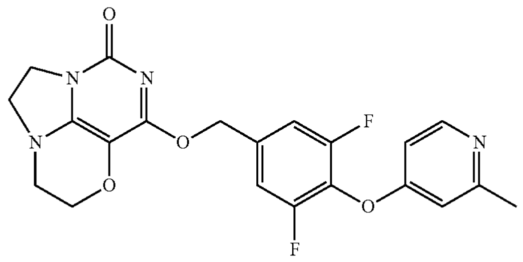
-continued
7
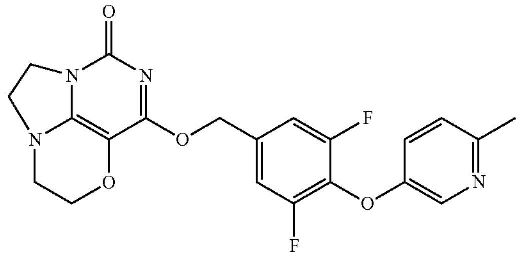
8
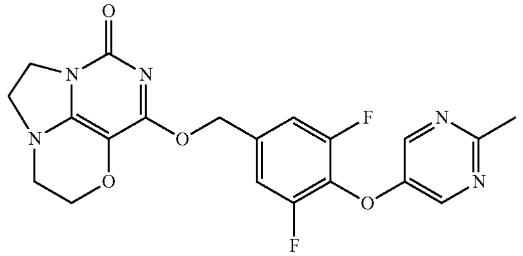
9
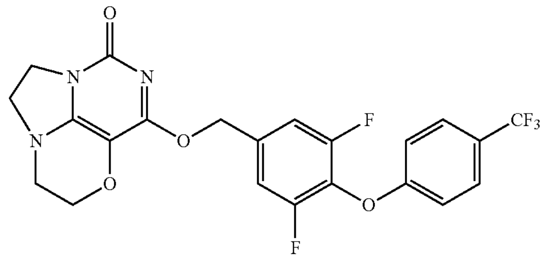
10
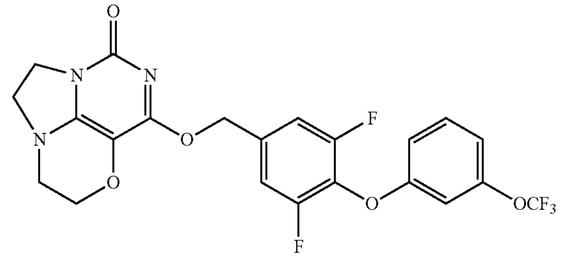
11
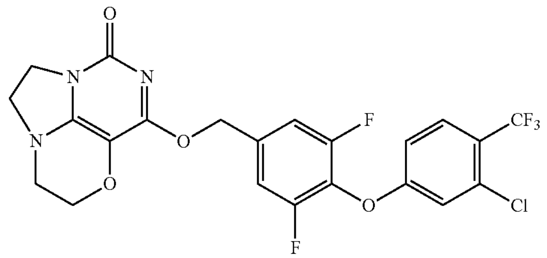
12
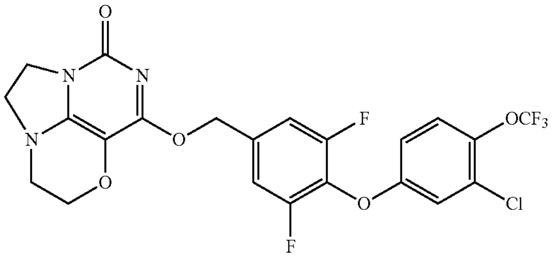

-continued

13

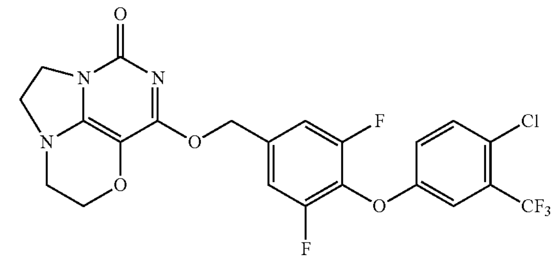

14

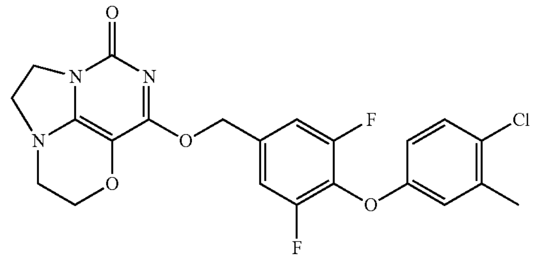

15

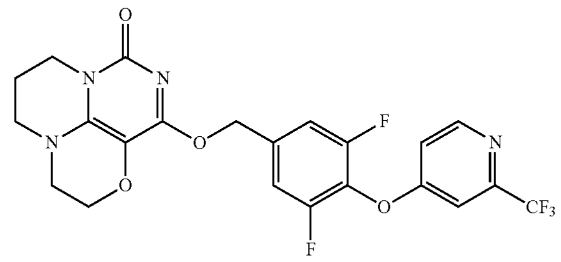

16

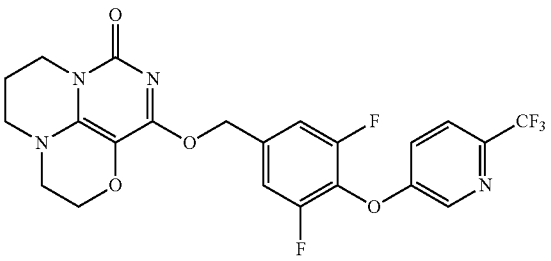

17

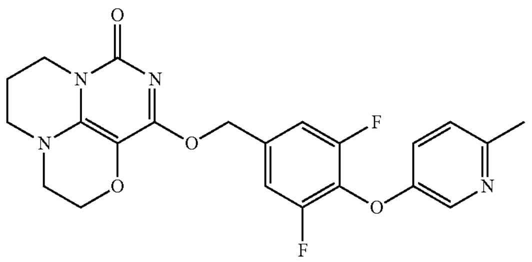

18

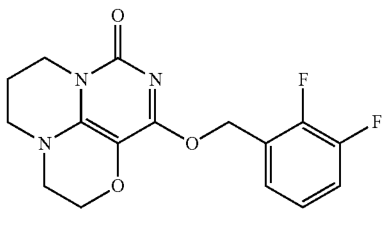

-continued

19

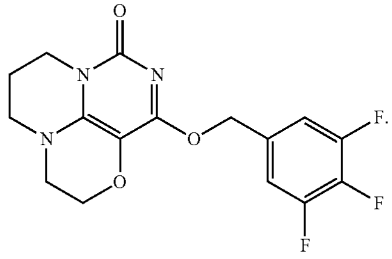

Optionally, the compound of formula (I) or its tautomers, mesoforms, racemates, enantiomers, diastereoisomers, or mixtures thereof, or pharmaceutically acceptable salts, include anionic salts and cationic salts of compounds of formula (I);

- optionally, the pharmaceutically acceptable salt includes alkali metal salt, alkaline earth metal salt, or ammonium salt of the compound of Formula (I); optionally, the alkali metal includes sodium, potassium, lithium, or cesium, and the alkaline earth metal includes magnesium, calcium, or strontium;
- optionally, the pharmaceutically acceptable salt comprises a compound of formula I or its tautomer, mesoform, racemate, enantiomer, diastereoisomer, or a mixture with an organic base;
- optionally, the organic base includes trialkylamine, pyridine, quinoline, piperidine, imidazole, picoline, dimethylaminopyridine, dimethylaniline, N-alkylmorpholine, 1,5-diazabicyclo[4.3.0]nonene-5,1,8-diazabicyclo [5.4.0]undecene-7,1,4-diazabicyclo[2.2.2]octane; alternatively, all Described trialkylamine comprises trimethylamine, triethylamine, N-ethyldiisopropylamine; Optionally, described N-alkylmorpholine comprises N-methylmorpholine;
- optionally, the pharmaceutically acceptable salt comprises a compound of formula I or its tautomer, mesoform, racemate, enantiomer, diastereoisomer, or a mixture with an an acid;
- optionally, the acid includes inorganic acid, organic acid; optionally, the inorganic acid includes hydrochloric acid, hydrobromic acid, hydroiodic acid, sulfuric acid, nitric acid, phosphoric acid, carbonic acid; optionally, the organic acid includes formic acid, acetic acid, Propionic acid, oxalic acid, malonic acid, succinic acid, fumaric acid, maleic acid, lactic acid, malic acid, citric acid, citric acid, tartaric acid, carbonic acid, picric acid, methanesulfonic acid, ethanesulfonic acid, p-toluenesulfonic acid acid, glutamic acid, pamoic acid In another aspect, there is provided a preparation method of a compound of Formula (I) or a pharmaceutically acceptable salt thereof, comprising the step of reacting a compound of Formula (II) with a compound of Formula (III) to produce the compound of Formula (I):

In another aspect, there is provided a preparation method of compound of formula (I) or its tautomer, mesomer, racemate, enantiomer, diastereoisomer, or a mixture thereof, or the pharmaceutically acceptable salt. The method is shown as the below reaction scheme:

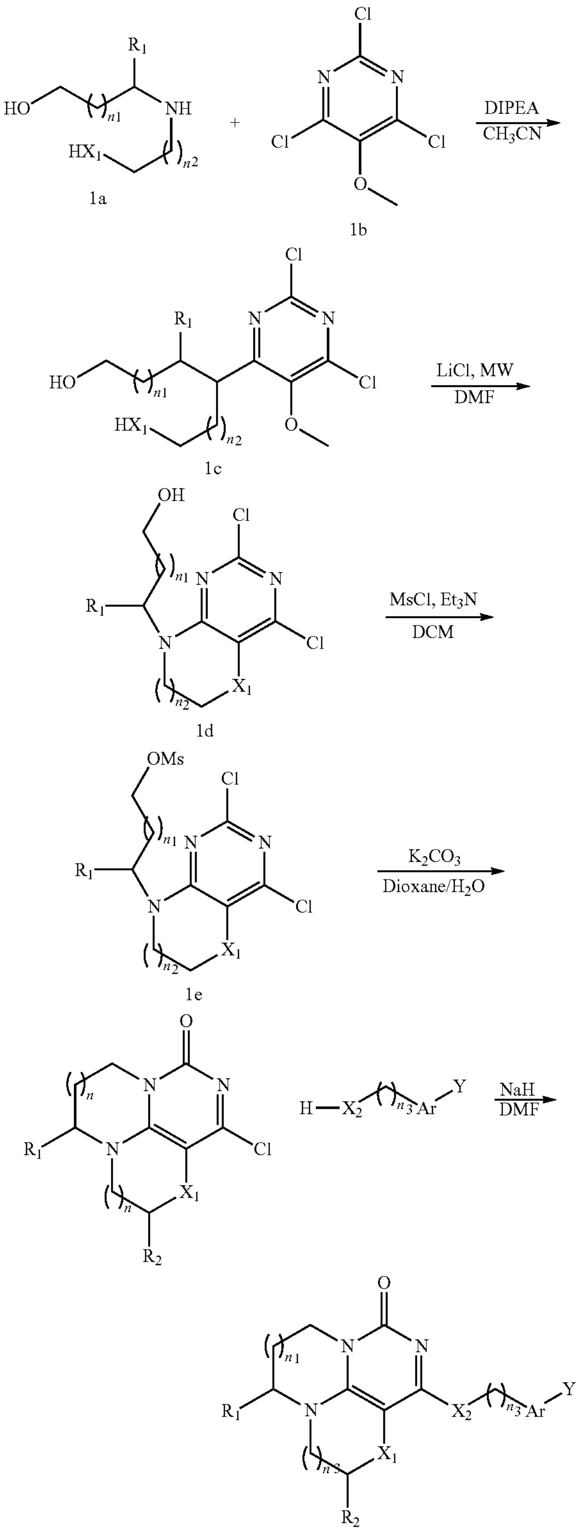

In each of the formulas in the preparation method described above, $n_1$, $n_2$, $n_3$, $R_1$, $R_2$, $X_1$, $X_2$, Ar, and Y are defined as above.

There are no specific limitations for the above reaction conditions. All the reactions can be carried out under conventional conditions.

In another aspect, there is provided a pharmaceutical composition, comprising a therapeutically effective amount of one or more of the compound of Formula (I) or a pharmaceutically acceptable salt thereof, and optionally, a pharmaceutically acceptable excipient(s).

In another aspect, a pharmaceutical composition is provided, which comprises a therapeutically effective amount of the above-mentioned compound of formula (I) or its tautomer, mesoform, racemate, enantiomer, diastereomer One or more of isomers, or a mixture thereof, or a pharmaceutically acceptable salt thereof, and optionally a pharmaceutically acceptable carrier.

Optionally, the dosage form of the pharmaceutical composition includes oral, rectal, or parenteral formulation;
- optionally, the oral formulation includes solid or liquid formulation;
- optionally, the solid formulation includes tablet, powder, granule, or capsule;
- optionally, the liquid formulation includes aqueous or oily suspension, or syrup;
- optionally, the parenteral formulation includes solution for injection, or aqueous or oily suspension.

In another aspect, there is provided the above-mentioned compound of formula (I) or its tautomer, mesomer, racemate, enantiomer, diastereoisomer, or mixture thereof, or its pharmaceutically acceptable Salt, or the above-mentioned pharmaceutical composition in the preparation of Lp-PLA2 inhibitor.

In another aspect, there is provided the above-mentioned compound of formula (I) or its tautomer, mesomer, racemate, enantiomer, diastereoisomer, or mixture thereof, or its pharmaceutically acceptable Salt, or the above-mentioned pharmaceutical composition, in the preparation of a medicament for treatment of neurodegeneration-related diseases;
- optionally, the neurodegeneration-related diseases include Alzheimer's disease (AD), glaucoma, and age-related macular degeneration (AMD).

In another aspect, there is provided the above-mentioned compound of formula (I) or its tautomer, mesomer, racemate, enantiomer, diastereoisomer, or mixture thereof, or its pharmaceutically acceptable Salt, or the above-mentioned pharmaceutical composition, in the preparation of a medicament for the treatment of cardiovascular diseases, diabetic macular edema (DME), or prostate diseases
- optionally, the cardiovascular diseases include atherosclerosis.

Beneficial effects of the present disclosure are as follows:

The compound of Formula (I) is an tricyclic pyrimidinone compound as an novel Lp-PLA2 inhibitor. It can be used to treat neurodegenerative related diseases such as Alzheimer's disease (AD), glaucoma and age-related macular degeneration (AMD), or cardiovascular diseases including atherosclerosis.

DETAILED DESCRIPTION

The present invention is further illustrated by the following examples. It should be understood that the embodiments herein are only used to illustrate the present invention, and do not limit the scope of the present invention in any way.

The starting materials of the present invention can be synthesized by a method known in the art, or be purchased from ABCR GmbH & Co. KG, Acros Organics, Aldrich Chemical Company, Accela ChemBio Inc., and Darry Chemicals, among other companies.

Unless otherwise specified, the solution in the examples refers to an aqueous solution.

Unless otherwise specified, the temperature in the examples at which the reaction is carried out is room temperature, e.g., 20° C. to 30° C.

Example 1 Preparation of Compound 1

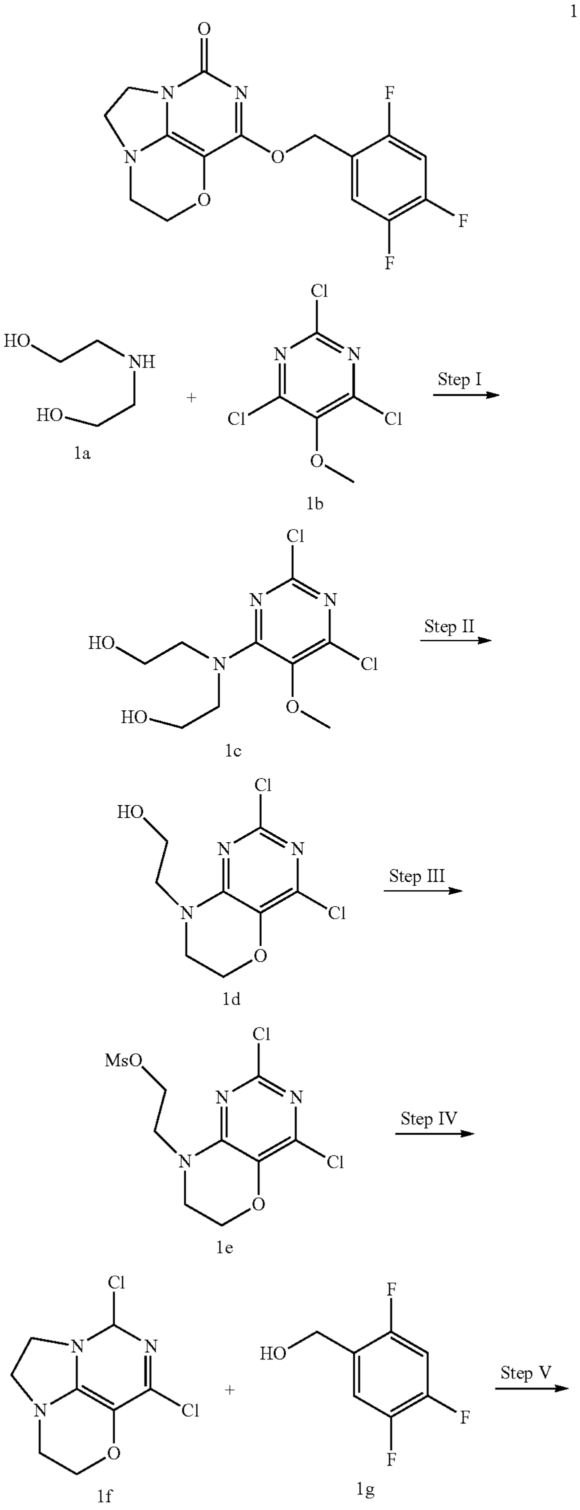

-continued

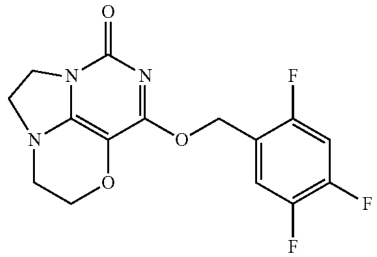

1

Step I: Preparation of Compound 1c

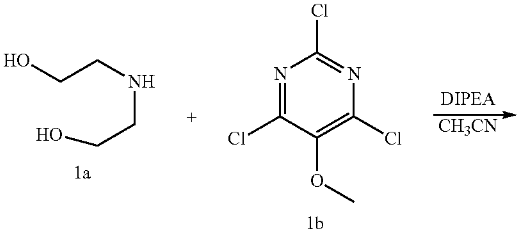

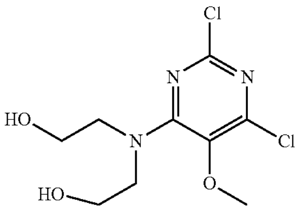

1c

At room temperature, 2,4,6-trichloro-5-methoxypyrimidine 1b (1.5 g, 7.03 mmol), diethanolamine 1a (1.1 g, 10.5 mmol) and diisopropylethylamine (1.36 g, 10.54 mmol) were dissolved in acetonitrile (50 mL), stirred and reacted for 3 h, concentrated under reduced pressure. Purification via silica gel column chromatography with an eluent system (dichloromethane/methanol=20/1) afforded the title compound 1c (1.6 g, Yield: 81.0%) as a white solid.

1H NMR (400 MHz, $CDCl_3$) δ3.94-3.89 (m, 4H), 3.88-3.83 (m, 4H), 3.77 (s, 3H), 3.17 (s, 2H).

Step II: Preparation of Compound 1d

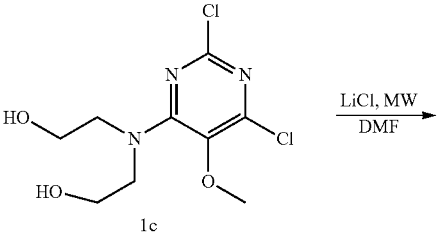

-continued

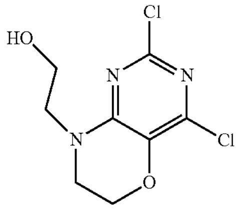

1d

At room temperature, chloro-5-methoxypyrimidine-4-yl) azanediyl)diethanol 1c (1.0 g, 3.54 mmol), and lithium chloride (0.75 g, 17.73 mmol) were dissolved in N,N-dimethylformamide (5 mL), heated in microwave at 130° C. for 1 h, concentrated under reduced pressure, extracted with ethyl acetate (60 mL×3). The combined organic phases were washed with a saturated aqueous solution of sodium chloride, dried over anhydrous sodium sulfate, filtered to remove desiccant, concentrated under reduced pressure. Purification via silica gel column chromatography with an eluent system (dichloromethane/methanol=20/1) afforded the title compound 1d (0.39 g, Yield: 44.0%) as a white solid.

$^1$H NMR (400 MHz, $CDCl_3$) δ4.32-4.27 (m, 2H), 3.92 (m, 2H), 3.83-3.76 (m, 2H), 3.76-3.69 (m, 2H).

Steps III and IV: Preparation of Compound 1f

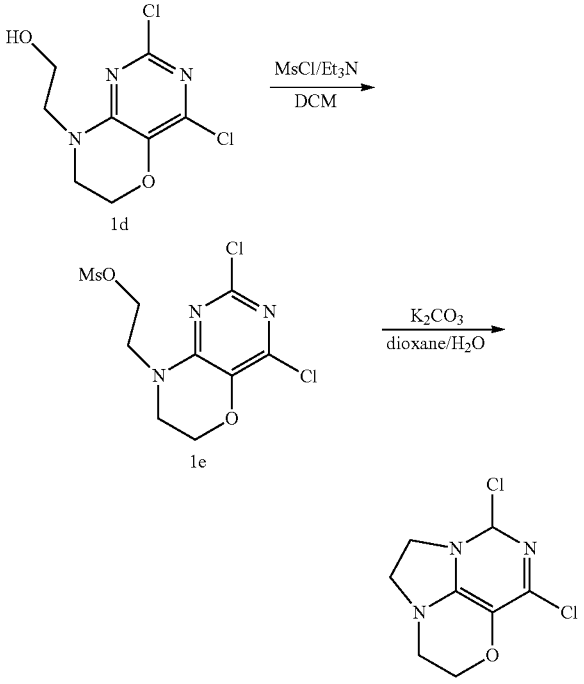

1d

1e

1f

At room temperature, 2-(2,4-dichloro-6hydro-pyrimido [5,4-b][1,4]oxazin-8(7H)-yl)ethanol 1d (0.77 g, 3.1 mmol) and Triethylamine (0.94 g, 9.3 mmol) were dissolved in dichloromethane (30 mL), then methanesulfonyl chloride (0.39 g, 3.4 mmol) was added dropwise at 0° C. The reaction was stirred and reacted at 0° C. for 1 h, concentrated and proceeded directly to the next reaction. The crude product was dissolved in a mixed solvent of 1/1 dioxane/water (60 mL), followed by addition of potassium carbonate (1.3 g, 9.3 mmol) at room temperature. The reaction mixture was stirred at 90° C. overnight, concentrated under reduced pressure. Purification via silica gel column chromatography with an eluent system (dichloromethane/methanol=10/1) afforded the title compound 1f (0.38 g, Yield: 57.4%) as a white solid.

$^1$H NMR (400 MHz, MeOD) δ4.32-4.25 (m, 2H), 4.25-4.17 (m, 2H), 3.99 (m, 2H), 3.60-3.52 (m, 2H).

Step V: Preparation of Compound 1

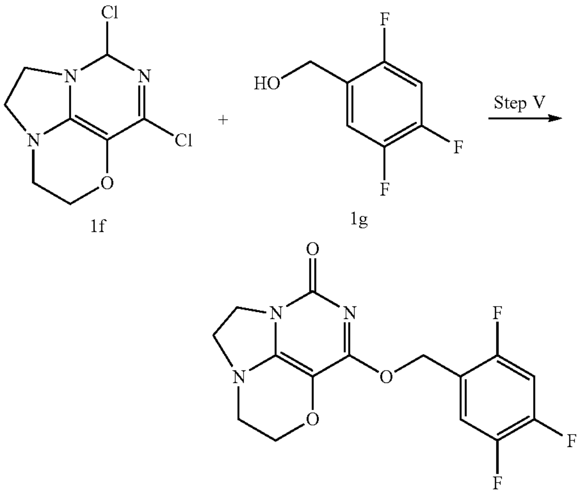

1f

1g

1

To a solution of (2,4,5-trifluorophenoxy)methanol 1g (39 mg, 0.24 mmol) in dry N,N-dimethylformamide (5 mL) was added sodium hydride (60% in mineral oil, 16 mg, 0.4 mmol) at 0° C., and stirred at room temperature for 5 min. Then compound 1f (43 mg, 0.20 mmol) was added, and stirred for 1 h, quenched with a small amount of water. Purification via silica gel column chromatography with an eluent system (dichloromethane/methanol=10/1) afforded the title compound 1 (13.6 mg, 20%) as a white solid.

$^1$H NMR (400 MHz, $CDCl_3$) δ7.30 (m, 1H), 6.96 (m, 1H), 5.43 (s, 2H), 4.32-4.22 (m, 2H), 4.20 (m, 2H), 3.78 (m, 2H), 3.48-3.39 (m, 2H). MS (ESI): m/z 340.1 $[M+H]^+$.

Example 2 Preparation of Compound 2

2

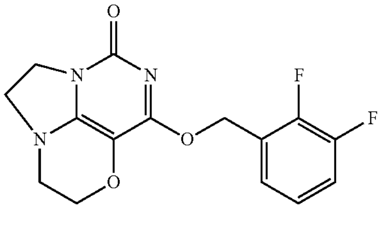

To a solution of (2,3-Difluorophenyl)methanol (35 mg, 0.24 mmol) in dry N,N-dimethylformamide (5 mL) was added sodium hydride (60% in mineral oil, 16 mg, 0.4 mmol) at 0° C., and stirred at room temperature for 5 min. Then compound 1f (43 mg, 0.20 mmol) was added, and stirred for 1 h, quenched with a small amount of water. Purification via silica gel column chromatography with an eluent system (dichloromethane/methanol=10/1) afforded the title compound 1 (15 mg, 23.3%) as a white solid.

$^1$H NMR (400 MHz, $CDCl_3$) δ7.45 (m, 1H), 6.96-6.82 (m, 2H), 5.43 (s, 2H), 4.33-4.22 (m, 2H), 4.19 (m, 2H), 3.77 (m, 2H), 3.46-3.39 (m, 2H). MS (ESI): m/z 322.1 $[M+H]^+$.

Example 3 Preparation of Compound 3

3

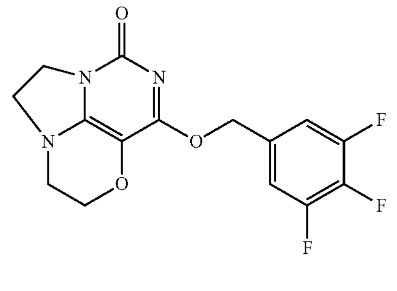

To a solution of (3,4,5-Trifluorophenyl)methanol (39 mg, 0.24 mmol) in dry N,N-dimethylformamide (5 mL) was added sodium hydride (60% in mineral oil, 16 mg, 0.4 mmol) at 0° C., and stirred at room temperature for 5 min. Then compound 1f (43 mg, 0.20 mmol) was added, and stirred for 1 h, quenched with a small amount of water. Purification via silica gel column chromatography with an eluent system (dichloromethane/methanol=10/1) afforded the title compound 3 (11.5 mg, 17%) as a white solid.

1H NMR (400 MHz, $CDCl_3$) δ7.31 (m, 2H), 5.42 (s, 2H), 4.31-4.22 (m, 2H), 4.20 (m, 2H), 3.78 (m, 2H), 3.46-3.38 (m, 2H). MS (ESI): m/z 340.1 $[M+H]^+$.

Example 4 Preparation of Compound 4

4

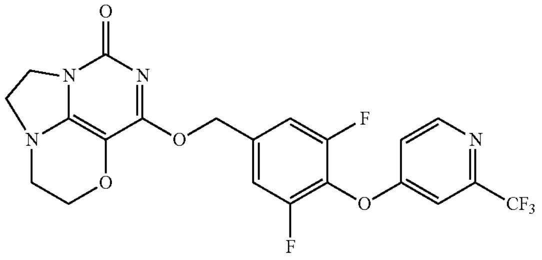

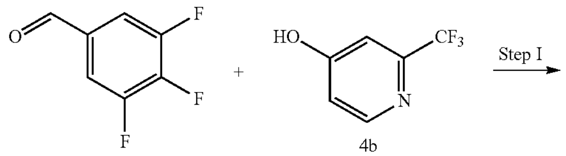

4a

4b

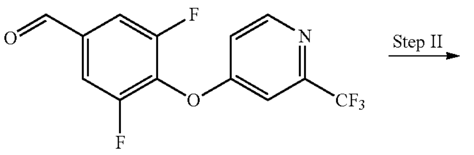

4c

-continued

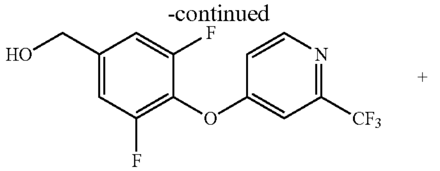

4d

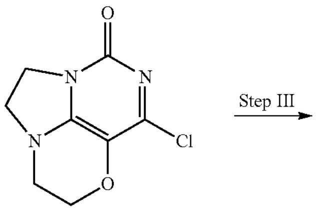

1f

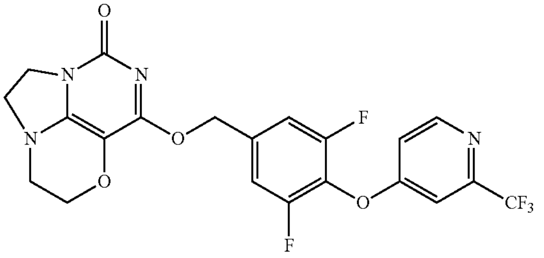

4

Step I: Preparation of Compound 4c 2-(Trifluoromethyl)pyridin-4-ol 4b (0.85 g, 5.2 mmol), 3,4,5-trifluorobenzaldehyde 4a (1 g, 6.2 mmol) and potassium carbonate (0.93 g, 6.76 mmol) were dissolved in N,N-dimethylformamide (DMF) (30 mL) at room temperature. The reaction mixture was stirred at 90° C. for 1 h, cooled to room temperature, followed by addtion of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=5/1) afforded the title compound 4c (1.47 g, yield: 93.2%) as a yellow solid.

$^1$H NMR (400 MHz, $CDCl_3$) δ9.97 (s, 1H), 8.65 (m, 1H), 7.63 (m, 2H), 7.27 (m, 1H), 7.01 (m, 1H).

Step II: Preparation of Compound 4d

At room temperature, 3,5-difluoro-4-((2-(trifluoromethyl) pyridin-4-yl)oxy)benzaldehyde 4c (1.47 g, 4.85 mmol) was dissolved in ethanol (50 mL), then $NaBH_4$ (184 mg, 4.84 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous Sodium sulfate, filtered to remove desiccant. The filtrate was concentrated under reduced pressure. Purification via silica gel column chromatography with an eluent system (petroleum ether/ethyl acetate=2/1) afforded the title compound 4d (1.04 g, yield: 70.3%) as a white solid.

$^1$H NMR (400 MHz, $CDCl_3$) δ8.59 (m, 1H), 7.24 (m, 1H), 7.11 (m, 2H), 6.99 (m, 1H), 4.75 (m, 2H), 2.19 (m, 1H).

Step III: Preparation of Compound 4

To a solution of (3,5-Difluoro-4-((2-(trifluoromethyl) pyridin-4-yl)oxy)phenyl)methanol 4d (68 mg, 0.22 mmol) in dry N,N-dimethylformamide (5 mL) was added sodium hydride (60% in mineral oil, 16 mg, 0.4 mmol) at 0° C., and stirred at room temperature for 5 min. Then compound 1f (43 mg, 0.20 mmol) was added, and stirred for 1 h, quenched with a small amount of water. Purification via silica gel column chromatography with an eluent system (dichloromethane/methanol=10/1) afforded the title compound 4 (31 mg, 32.1%) as a white solid.

$^1$H NMR (400 MHz, $CDCl_3$) δ8.58 (m, 1H), 7.24 (m, 1H), 7.16 (m, 2H), 6.96 (m, 1H), 5.45 (s, 2H), 4.32-4.23 (m, 2H), 4.19 (m, 2H), 3.78 (m, 2H), 3.46-3.37 (m, 2H). MS (ESI): m/z 482.9 $[M+H]^+$.

Example 5 Preparation of Compound 5

5

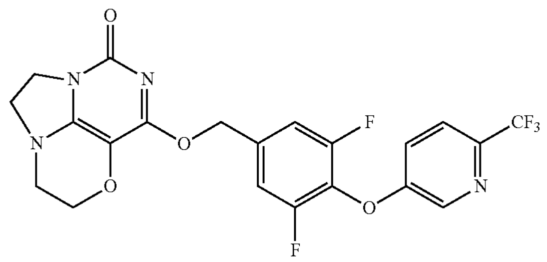

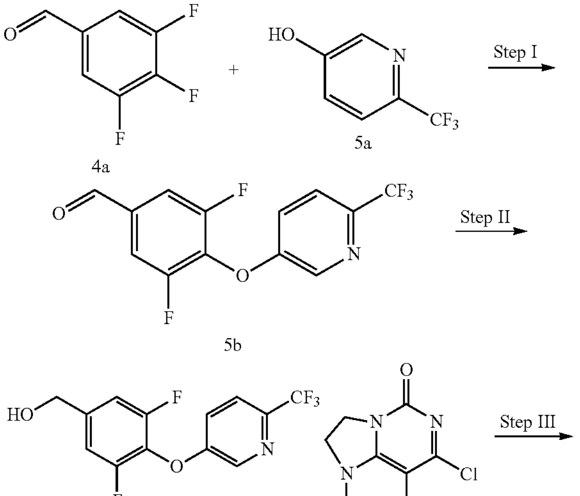

4a 5a 5b 5c 1f 5

Step I: Preparation of Compound 5b 6-(trifluoromethyl)pyridin-3-ol 5a (0.85 g, 5.2 mmol), 3,4,5-trifluorobenzaldehyde 4a (1 g, 6.2 mmol) and potassium carbonate (0.93 g, 6.76 mmol) were dissolved in N,N-dimethylformamide (DMF) (30 mL) at room temperature. The reaction mixture was stirred at 90° C. for 1 h, cooled to room temperature, followed by addition of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=5/1) afforded the title compound 5b (1.34 g, yield: 85.0%) as a yellow solid.

Step II: Preparation of Compound 5c

At room temperature, 3,5-Difluoro-4-((6-(trifluoromethyl)pyridin-3-yl)oxy)benzaldehyde 5b (1.34 g, 4.4 mmol) was dissolved in ethanol (50 mL), then $NaBH_4$ (167 mg, 4.4 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=2/1) afforded the title compound 5c (0.77 g, yield: 57.3%) as a colorless oil.

$^1$H NMR (400 MHz, $CDCl_3$) δ8.46 (m, 1H), 7.63 (m, m 1H), 7.30 (m, 1H), 7.09 (m, 2H), 4.73 (m, 2H), 2.40 (m, 1H).

Step III: Preparation of Compound 5

To a solution of (3,5-Difluoro-4-((6-(trifluoromethyl) pyridin-3-yl)oxy)phenyl)methanol 5c (43 mg, 0.14 mmol) in dry N,N-dimethylformamide (5 mL) was added sodium hydride (60% in mineral oil, 11 mg, 0.28 mmol) at 0° C., and stirred at room temperature for 5 min. Then compound 1f (30 mg, 0.14 mmol) was added, and stirred for 1 h, quenched with a small amount of water. Purification via silica gel column chromatography with an eluent system (dichloromethane/methanol=10/1) afforded the title compound 5 (11 mg, 16.3%) as a white solid.

$^1$H NMR (400 MHz, $CDCl_3$) δ8.50 (m, 1H), 7.63 (m, 1H), 7.28 (m, m 1H), 7.15 (m, 2H), 5.45 (s, 2H), 4.33-4.27 (m, 2H), 4.20 (m, 2H), 3.78 (m, 2H), 3.46-3.39 (m, 2H). MS (ESI): m/z 482.9 $[M+H]^+$.

Example 6 Preparation of Compound 6

6

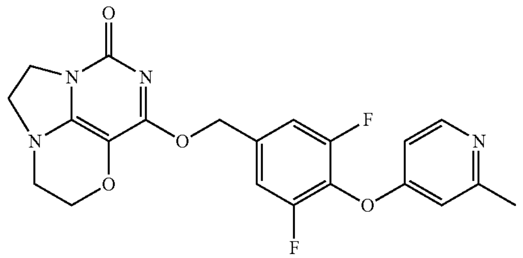

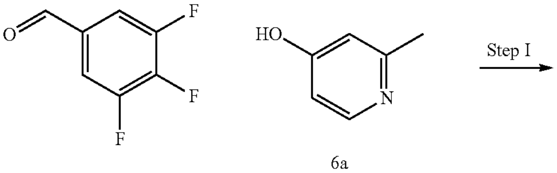

4a 6a

-continued

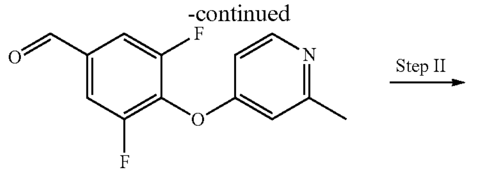

6b

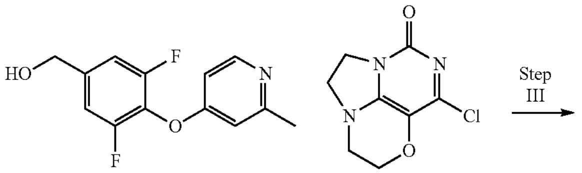

6c 1f

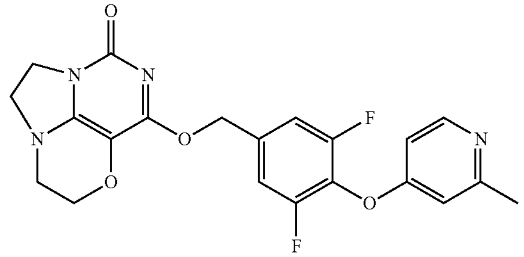

6

Step I: Preparation of Compound 6b

6-Methylpyridin-4-ol 6a (0.5 g, 4.6 mmol), 3,4,5-trifluorobenzaldehyde 4a (0.88 g, 5.5 mmol) and potassium carbonate (0.82 g, 5.95 mmol) were dissolved in N,N-dimethylformamide (DMF) (30 mL) at room temperature. The reaction mixture was stirred at 90° C. for 2 h, cooled to room temperature, followed by addtion of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 6b (0.4 g, yield: 34.8%) as a yellow solid.

$^1$H NMR (400 MHz, $CDCl_3$) δ9.94 (m, 1H), 8.39 (m, 1H), 7.63-7.55 (m, 2H), 6.72-6.64 (m, 2H), 2.50 (s, 3H).

Step II: Preparation of Compound 6c

At room temperature, 3,5-Difluoro-4-((2-methylpyridin-4-yl)oxy)benzaldehyde 6b (0.4 g, 1.6 mmol) was dissolved in ethanol (50 mL), then $NaBH_4$ (71 mg, 1.87 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 6c (0.34 g, yield: 85.7%) as a colorless oil.

$^1$H NMR (400 MHz, $CDCl_3$) δ8.29 (m, 1H), 7.07 (m, 2H), 6.70 (m, 1H), 6.65 (m, 1H), 4.73 (s, 2H), 3.20 (m, 1H), 2.50 (s, 3H).

Step III: Preparation of Compound 6

To a solution of (3,5-Difluoro-4-((2-methylpyridin-4-yl)oxy)phenyl)methanol 6c (35 mg, 0.14 mmol) in dry N,N-dimethylformamide (5 mL) was added sodium hydride (60% in mineral oil, 11 mg, 0.28 mmol) at 0° C., and stirred at room temperature for 5 min. Then compound 1f (30 mg, 0.14 mmol) was added, and stirred for 1 h, quenched with a small amount of water. Purification via silica gel column chromatography with an eluent system (dichloromethane/methanol=10/1) afforded the title compound 6 (6 mg, 10%) as a white solid.

$^1$H NMR (400 MHz, $CDCl_3$) δ8.35 (m, 1H), 7.12 (m, 2H), 6.67 (m, 2H), 5.44 (s, 2H), 4.33-4.27 (m, 2H), 4.19 (m, 2H), 3.78 (m, 2H), 3.45-3.38 (m, 2H), 2.50 (s, 3H). MS (ESI): m/z 429.0 $[M+H]^+$.

Example 7 Preparation of Compound 7

7

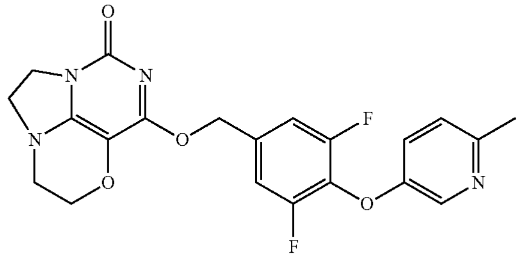

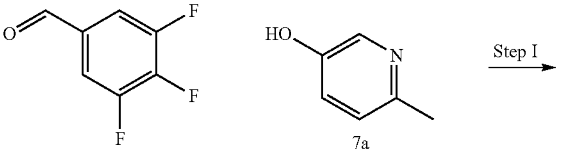

4a 7a

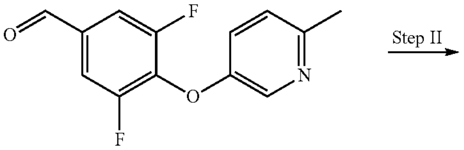

7b

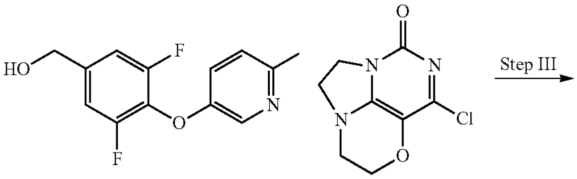

7c 1f

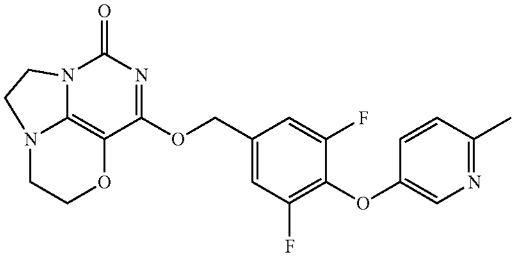

7

Step I: Preparation of Compound 7b

6-Methylpyridin-3-ol 7a (0.57 g, 5.2 mmol), 3,4,5-trifluorobenzaldehyde 4a (1 g, 6.2 mmol) and potassium carbonate (0.93 g, 6.76 mmol) were dissolved in N,N-dimethylformamide (DMF) (30 mL) at room temperature. The reaction mixture was stirred at 90° C. for 1 h, cooled to room temperature, followed by addtion of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 7b (0.91 g, yield: 70.2%) as a yellow solid.

$^1$H NMR (400 MHz, $CDCl_3$) δ9.92 (s, 1H), 8.28 (s, 1H), 7.62-7.49 (m, 2H), 7.18-7.10 (m, 2H), 2.54 (s, 3H).

Step II: Preparation of Compound 7c

At room temperature, 3,5-Difluoro-4-((6-methylpyridin-3-yl)oxy)benzaldehyde 7b (0.91 g, 3.6 mmol) was dissolved in methanol (50 mL), then $NaBH_4$ (161 mg, 4.2 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 7c (0.89 g, yield: 98.4%) as a colorless oil.

$^1$H NMR (400 MHz, $CDCl_3$) δ8.20 (m, 1H), 7.16-6.98 (m, 4H), 4.69 (m, 2H), 2.88 (m, 1H), 2.50 (s, 3H).

Step III: Preparation of Compound 7

To a solution of (3,5-Difluoro-4-((6-methylpyridin-3-yl)oxy)phenyl)methanol 7c (35 mg, 0.14 mmol) in dry N,N-dimethylformamide (5 mL) was added sodium hydride (60% in mineral oil, 11 mg, 0.28 mmol) at 0° C., and stirred at room temperature for 5 min. Then compound 1f (30 mg, 0.14 mmol) was added, and stirred for 1 h, quenched with a small amount of water. Purification via silica gel column chromatography with an eluent system (dichloromethane/methanol=10/1) afforded the title compound 7 (12 mg, 20%) as a white solid.

$^1$H NMR (400 MHz, $CDCl_3$) δ8.27 (m, 1H), 7.14-7.02 (m, 4H), 5.42 (s, 2H), 4.32-4.25 (m, 2H), 4.19 (m, 2H), 3.77 (m, 2H), 3.45-3.36 (m, 2H), 2.51 (s, 3H). MS (ESI): m/z 429.0 [M+H]$^+$.

Example 8 Preparation of Compound 8

8

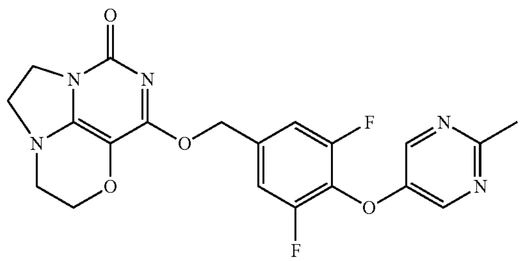

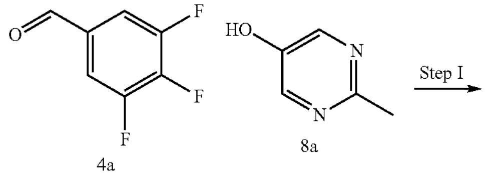

4a

8a

-continued

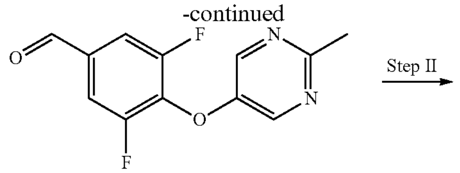

8b

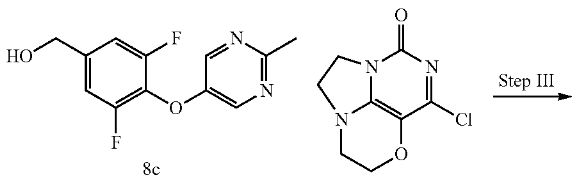

8c

1f

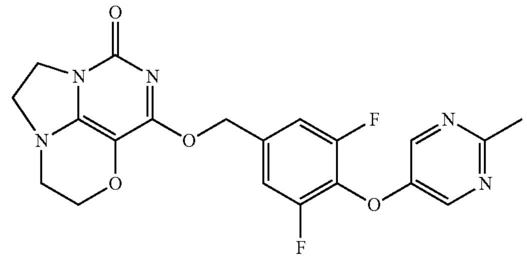

8

Step I: Preparation of Compound 8b 2-methylpyrimidin-5-ol 8a (0.25 g, 2.3 mmol), 3,4,5-trifluorobenzaldehyde 4a (0.44 g, 2.7 mmol) and potassium carbonate (0.41 g, 2.9 mmol) were dissolved in N,N-dimethylformamide (DMF) (30 mL) at room temperature. The reaction mixture was stirred at 90° C. for 2 h, cooled to room temperature, followed by addtion of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 8b (0.24 g, yield: 41.7%) as a yellow solid.

$^1$H NMR (400 MHz, $CDCl_3$) δ9.93 (s, 1H), 8.39 (s, 2H), 7.64-7.54 (m, 2H), 2.72 (s, 3H).

Step II: Preparation of Compound 8c

At room temperature, 3,5-Difluoro-4-((2-methylpyrimidin-5-yl)oxy)benzaldehyde 8b (0.24 g, 0.96 mmol) was dissolved in methanol (50 mL), then $NaBH_4$ (30 mg, 0.79 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 8c (0.17 g, yield: 70.2%) as a colorless oil.

$^1$H NMR (400 MHz, $CDCl_3$) δ8.33 (s, 2H), 7.04 (m, 2H), 4.71 (m, 2H), 2.70 (s, 3H).

Step III: Preparation of Compound 8

To a solution of (3,5-Difluoro-4-((2-methylpyrimidin-5-yl)oxy)phenyl)methanol 8c (35 mg, 0.14 mmol) in dry N,N-dimethylformamide (5 mL) was added sodium hydride (60% in mineral oil, 11 mg, 0.28 mmol) at 0° C., and stirred at room temperature for 5 min. Then compound 1f (30 mg, 0.14 mmol) was added, and stirred for 1 h, quenched with a small amount of water. Purification via silica gel column chromatography with an eluent system (dichloromethane/methanol=10/1) afforded the title compound 8 (8 mg, 13.3%) as a white solid.

$^1H$ NMR (400 MHz, $CDCl_3$) δ8.34 (s, 2H), 7.13 (m, 2H), 5.43 (s, 2H), 4.32-4.24 (m, 2H), 4.19 (m, 2H), 3.77 (m, 2H), 3.42 (m, 2H), 2.69 (s, 3H). MS (ESI): m/z 429.9 [M+H]$^+$.

Example 9 Preparation of Compound 9

9

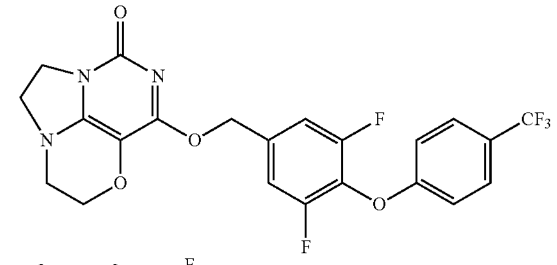

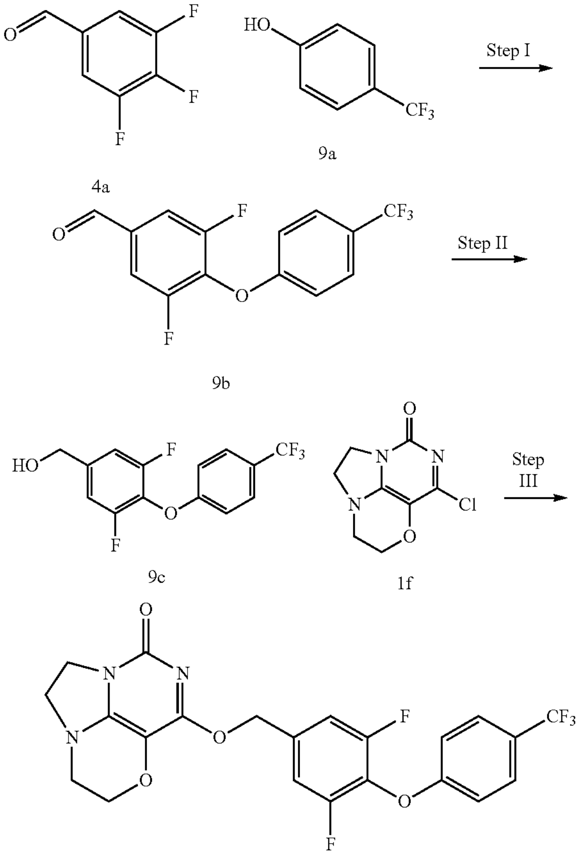

4a 9a 9b 9c 1f 9

Step I: Preparation of Compound 9b 4-(Trifluoromethyl)phenol 9a (0.84 g, 5.2 mmol), 3,4,5-trifluorobenzaldehyde 4a (1 g, 6.2 mmol) and potassium carbonate (0.93 g, 6.76 mmol) were dissolved in N,N-dimethylformamide (DMF) (30 mL) at room temperature. The reaction mixture was stirred at 90° C. for 1 h, cooled to room temperature, followed by addtion of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=5/1) afforded the title compound 9b (1.33 g, yield: 84.6%) as a yellow solid.

$^1H$ NMR (400 MHz, $CDCl_3$) δ9.94 (m, 1H), 7.59 (m, 4H), 7.04 (m, 2H).

Step II: Preparation of Compound 9c

At room temperature, 3,5-Difluoro-4-(4-(trifluoromethyl)phenoxy)benzaldehyde 9b (1.33 g, 4.4 mmol) was dissolved in methanol (50 mL), then $NaBH_4$ (166 mg, 4.4 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=2/1) afforded the title compound 9c (0.85 g, yield: 63.4%) as a colorless oil.

$^1H$ NMR (400 MHz, $CDCl_3$) δ7.57 (m, 2H), 7.09-7.00 (m, 4H), 4.72 (m, 2H), 2.03 (m, 1H).

Step III: Preparation of Compound 9

To a solution of 3,5-Difluoro-4-(4-(trifluoromethyl)phenoxy)phenyl)methanol 9c (43 mg, 0.14 mmol) in dry N,N-dimethylformamide (5 mL) was added sodium hydride (60% in mineral oil, 11 mg, 0.28 mmol) at 0° C., and stirred at room temperature for 5 min. Then compound 1f (30 mg, 0.14 mmol) was added, and stirred for 1 h, quenched with a small amount of water. Purification via silica gel column chromatography with an eluent system (dichloromethane/methanol=10/1) afforded the title compound 9 (9 mg, 13.4%) as a white solid.

$^1H$ NMR (400 MHz, $CDCl_3$) δ7.56 (m, 2H), 7.16-7.09 (m, 2H), 7.00 (m, 2H), 5.44 (s, 2H), 4.30 (m, 2H), 4.20 (m, 2H), 3.78 (m, 2H), 3.46-3.35 (m, 2H). MS (ESI): m/z 481.9 [M+H]$^+$.

Example 10 Preparation of Compound 10

10

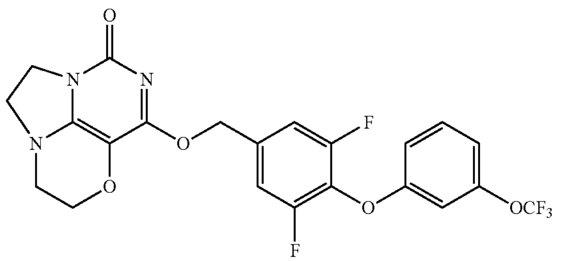

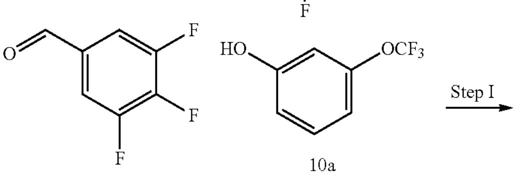

4a 10a

-continued

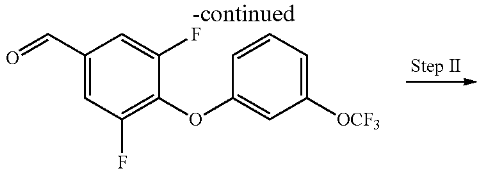

10b

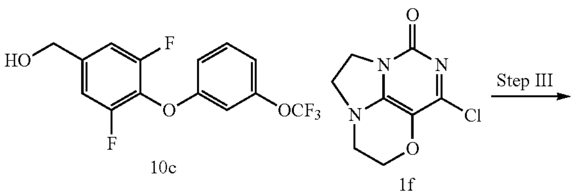

10c 1f

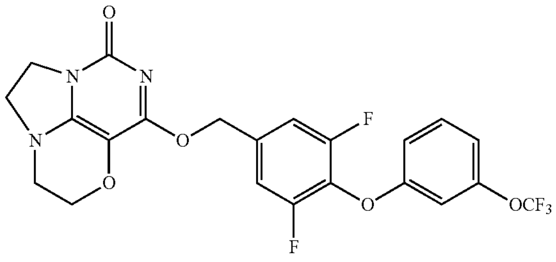

10

Step I: Preparation of Compound 10b 3-(Trifluoromethoxy)phenol 10a (0.50 g, 2.8 mmol), 3,4,5-trifluorobenzaldehyde 4a (0.5 g, 3.1 mmol) and potassium carbonate (0.5 g, 3.64 mmol) were dissolved in N,N-dimethylformamide (DMF) (30 mL) at room temperature. The reaction mixture was stirred at 90° C. for 2 h, cooled to room temperature, followed by addtion of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 10b (0.73 g, yield: 81.9%) as a yellow solid.

$^1$H NMR (400 MHz, $CDCl_3$) δ9.94 (s, 1H), 7.64-7.54 (m, 2H), 7.34 (m, 1H), 7.00 (m, 1H), 6.87 (m, 2H).

Step II: Preparation of Compound 10c

At room temperature, 4-(3-(Trifluoromethoxy)phenoxy)-3,5-difluorobenzaldehyde 10b (0.73 g, 2.3 mmol) was dissolved in methanol (50 mL), then $NaBH_4$ (86 mg, 2.26 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 10c (0.57 g, yield: 77.4%) as a colorless oil.

$^1$H NMR (400 MHz, $CDCl_3$) δ7.30 (m, 1H), 7.06 (m, 2H), 6.94 (m, 1H), 6.85 (m, 1H), 6.81 (s, 1H), 4.72 (m, 2H), 1.94 (m, 1H).

Step III: Preparation of Compound 10

To a solution of 4-(3-(Trifluoromethoxy)phenoxy)-3,5-difluorophenyl)methanol 10c (48 mg, 0.15 mmol) in dry N,N-dimethylformamide (5 mL) was added sodium hydride (60% in mineral oil, 11 mg, 0.28 mmol) at 0° C., and stirred at room temperature for 5 min. Then compound 1f (30 mg, 0.14 mmol) was added, and stirred for 1 h, quenched with a small amount of water. Purification via silica gel column chromatography with an eluent system (dichloromethane/methanol=10/1) afforded the title compound 10 (18 mg, 25.8%) as a white solid.

$^1$H NMR (400 MHz, $CDCl_3$) δ7.30 (m, 1H), 7.11 (m, 2H), 6.93 (m, 1H), 6.83 (m, 2H), 5.44 (s, 2H), 4.34-4.27 (m, 2H), 4.20 (m, 2H), 3.78 (m, 2H), 3.46-3.38 (m, 2H). MS (ESI): m/z 497.9 $[M+H]^+$.

Example 11 Preparation of Compound 11

11

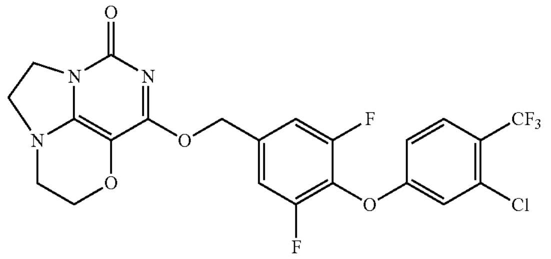

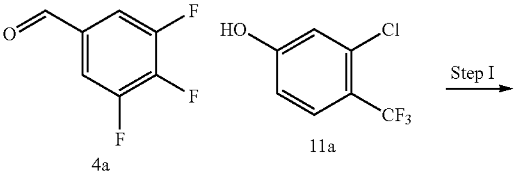

4a 11a

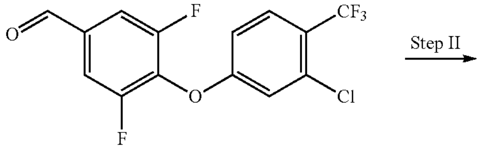

11b

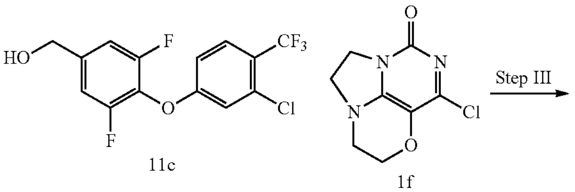

11c 1f

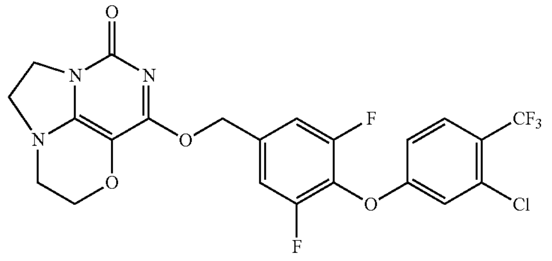

11

Step I: Preparation of Compound 11b

3-Chloro-4-(trifluoromethyl)phenol 11a (0.25 g, 1.27 mmol), 3,4,5-trifluorobenzaldehyde 4a (0.22 g, 1.4 mmol) and potassium carbonate (0.23 g, 1.65 mmol) were dissolved in N,N-dimethylformamide (DMF) (20 mL) at room temperature. The reaction mixture was stirred at 90° C. for 2 h, cooled to room temperature, followed by addtion of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 11b (0.32 g, yield: 74.8%) as a yellow solid.

$^1$H NMR (400 MHz, $CDCl_3$) δ9.95 (s, 1H), 7.69-7.56 (m, 3H), 7.10 (m, 1H), 6.92 (m, 1H).

Step II: Preparation of Compound 11c

At room temperature, 4-(3-Chloro-4-(trifluoromethyl)phenoxy)-3,5-difluorobenzaldehyde 11b (0.32 g, 0.95 mmol) was dissolved in methanol (50 mL), then $NaBH_4$ (36 mg, 0.95 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 11c (0.15 g, yield: 46.6%) as a white solid.

$^1$H NMR (400 MHz, $CDCl_3$) δ7.62 (m, 1H), 7.13-7.00 (m, 3H), 6.90 (m, 1H), 4.74 (m, 2H), 1.88 (m, 1H).

Step III: Preparation of Compound 11

To a solution of (4-(3-Chloro-4-(trifluoromethyl)phenoxy)-3,5-difluorophenyl)methanol 11c (67 mg, 0.20 mmol) in dry N,N-dimethylformamide (5 mL) was added sodium hydride (60% in mineral oil, 15 mg, 0.38 mmol) at 0° C., and stirred at room temperature for 5 min. Then compound 1f (40 mg, 0.19 mmol) was added, and stirred for 1 h, quenched with a small amount of water. Purification via silica gel column chromatography with an eluent system (dichloromethane/methanol=10/1) afforded the title compound 11 (21 mg, 21.4%) as a white solid.

$^1$H NMR (400 MHz, $CDCl_3$) δ7.62 (m, 1H), 7.14 (m, 2H), 7.06 (m, 1H), 6.89 (m, 1H), 5.45 (s, 2H), 4.34-4.26 (m, 2H), 4.21 (m, 2H), 3.78 (m, 2H), 3.52-3.37 (m, 2H). MS (ESI): m/z 515.9 [M+H]$^+$.

Example 12 Preparation of Compound 12

12

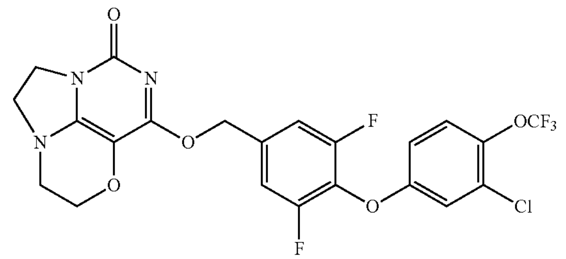

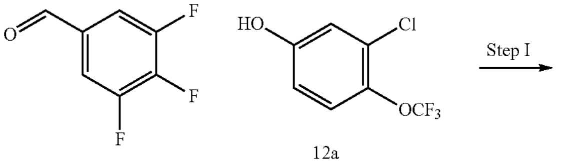

4a 12a

-continued

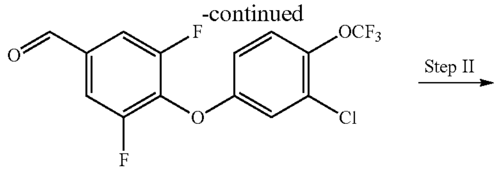

12b

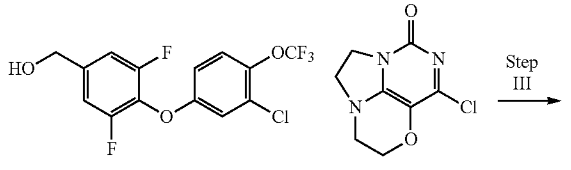

12c 1f

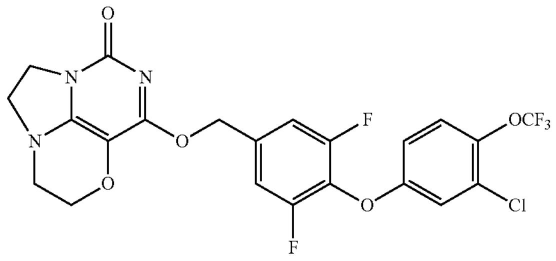

12

Step I: Preparation of Compound 12b

3-Chloro-4-(trifluoromethoxy)phenol 12a (0.5 g, 2.4 mmol), 3,4,5-trifluorobenzaldehyde 4a (0.41 g, 2.6 mmol) and potassium carbonate (0.42 g, 3.04 mmol) were dissolved in N,N-dimethylformamide (DMF) (20 mL) at room temperature. The reaction mixture was stirred at 90° C. for 2 h, cooled to room temperature, followed by addtion of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 12b (0.62 g, yield: 73.2%) as a yellow solid.

$^1$H NMR (400 MHz, $CDCl_3$) δ9.94 (s, 1H), 7.63-7.54 (m, 2H), 7.29 (m, 1H), 7.07 (m, 1H), 6.90 (m, 1H).

Step II: Preparation of Compound 12c

At room temperature, 4-(3-Chloro-4-(trifluoromethoxy)phenoxy)-3,5-difluorobenzaldehyde 12b (0.62 g, 1.8 mmol) was dissolved in methanol (50 mL), then $NaBH_4$ (62 mg, 1.63 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 12c (0.53 g, yield: 83.0%) as a colorless oil.

$^1$H NMR (400 MHz, $CDCl_3$) δ7.25 (m, 1H), 7.06 (m, 2H), 7.01 (m, 1H), 6.87 (m, 1H), 4.72 (s, 2H), 2.04 (m, 1H).

Step III: Preparation of Compound 12

To a solution of (4-(3-Chloro-4-(trifluoromethoxy)phenoxy)-3,5-difluorophenyl)methanol 12c (67 mg, 0.19 mmol) in dry N,N-dimethylformamide (5 mL) was added sodium hydride (60% in mineral oil, 15 mg, 0.38 mmol) at 0° C., and stirred at room temperature for 5 min. Then compound 1f (40 mg, 0.19 mmol) was added, and stirred for 1 h, quenched with a small amount of water. Purification via silica gel column chromatography with an eluent system (dichloromethane/methanol=10/1) afforded the title compound 12 (19 mg, 18.8%) as a white solid.

$^1$H NMR (400 MHz, $CDCl_3$) δ7.23 (m, 1H), 7.16-7.08 (m, 2H), 7.03 (m, 1H), 6.86 (m, 1H), 5.44 (s, 2H), 4.30 (m, 2H), 4.20 (m, 2H), 3.78 (m, 2H), 3.46-3.39 (m, 2H). MS (ESI): m/z 531.8 $[M+H]^+$.

Example 13 Preparation of Compound 13

13

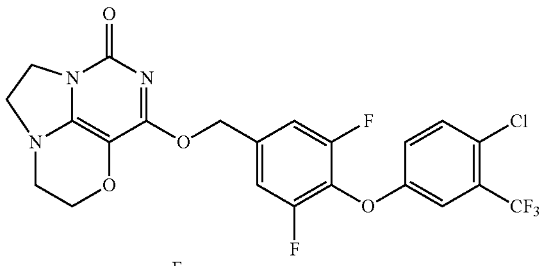

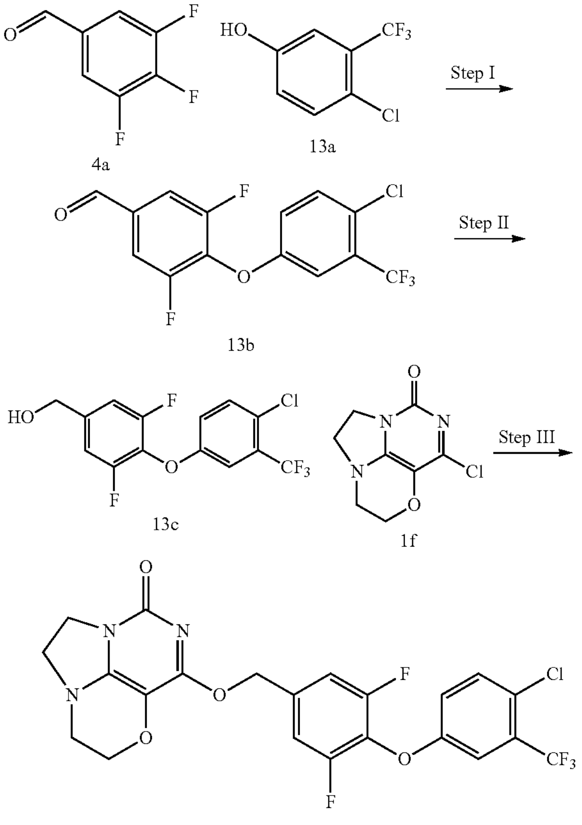

4a 13a 13b 13c 1f 13

Step I: Preparation of Compound 13b

4-Chloro-3-(trifluoromethyl)phenol 13a (0.5 g, 2.5 mmol), 3,4,5-trifluorobenzaldehyde 4a (0.41 g, 2.8 mmol) and potassium carbonate (0.46 g, 3.3 mmol) were dissolved in N,N-dimethylformamide (DMF) (30 mL) at room temperature. The reaction mixture was stirred at 90° C. for 2 h, cooled to room temperature, followed by addtion of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 13b (0.6 g, yield: 71.3%) as a yellow solid.

$^1$H NMR (400 MHz, $CDCl_3$) δ9.94 (s, 1H), 7.64-7.55 (m, 2H), 7.45 (m, 1H), 7.31 (m, 1H), 7.05 (m, 1H).

Step II: Preparation of Compound 13c

At room temperature, 4-(4-Chloro-3-(trifluoromethyl)phenoxy)-3,5-difluorobenzaldehyde 13b (0.6 g, 1.78 mmol) was dissolved in methanol (50 mL), then $NaBH_4$ (67 mg, 1.76 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 13c (0.28 g, yield: 46.4%) as a white solid.

$^1$H NMR (400 MHz, $CDCl_3$) δ7.41 (m, 1H), 7.28 (m, 1H), 7.08-7.00 (m, 3H), 4.73 (m, 2H), 1.94 (m, 1H).

Step III: Preparation of Compound 13

To a solution of (4-(4-Chloro-3-(trifluoromethyl)phenoxy)-3,5-difluorophenyl)methanol 13c (64 mg, 0.19 mmol) in dry N,N-dimethylformamide (5 mL) was added sodium hydride (60% in mineral oil, 15 mg, 0.38 mmol) at 0° C., and stirred at room temperature for 5 min. Then compound 1f (40 mg, 0.19 mmol) was added, and stirred for 1 h, quenched with a small amount of water. Purification via silica gel column chromatography with an eluent system (dichloromethane/methanol=10/1) afforded the title compound 13 (29 mg, 29.6%) as a white solid.

$^1$H NMR (400 MHz, $CDCl_3$) δ7.41 (m, 1H), 7.30 (m, 1H), 7.13 (m, 2H), 6.99 (m, 1H), 5.44 (s, 2H), 4.30 (m, 2H), 4.20 (m, 2H), 3.78 (m, 2H), 3.57-3.35 (m, 2H). MS (ESI): m/z 515.9 $[M+H]^+$.

Example 14 Preparation of Compound 14

14

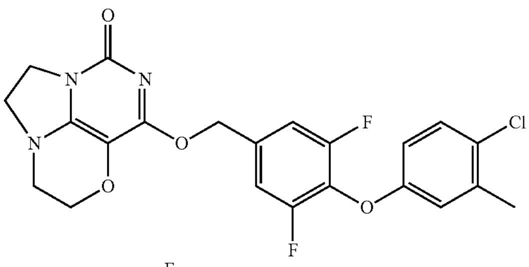

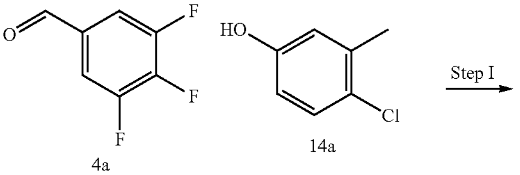

4a 14a

-continued

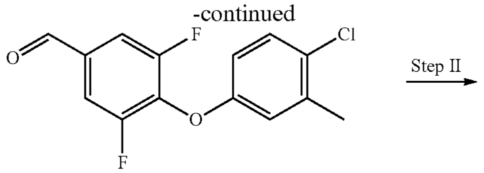

14b

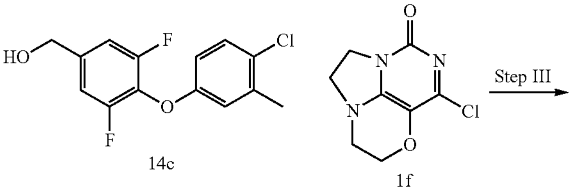

14c

1f

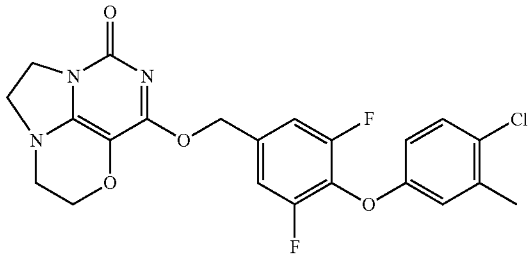

14

Step I: Preparation of Compound 14b 4-chloro-3-methylphenol 14a (1 g, 7.0 mmol), 3,4,5-trifluorobenzaldehyde 4a (1.2 g, 7.5 mmol) and potassium carbonate (1.3 g, 9.1 mmol) were dissolved in N,N-dimethylformamide (DMF) (30 mL) at room temperature. The reaction mixture was stirred at 90° C. for 2 h, cooled to room temperature, followed by addtion of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 14b (1.2 g, yield: 60.6%) as a yellow solid.

$^1$H NMR (400 MHz, $CDCl_3$) δ9.92 (s, 1H), 7.61-7.51 (m, 2H), 7.30-7.23 (m, 1H), 6.85 (m, 1H), 6.73 (m, 1H), 2.34 (s, 3H).

Step II: Preparation of Compound 14c

At room temperature, 4-(4-Chloro-3-methylphenoxy)-3,5-difluorobenzaldehyde 14b (1.2 g, 4.24 mmol) was dissolved in methanol (50 mL), then $NaBH_4$ (161 mg, 4.2 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 14c (0.89 g, yield: 73.7%) as a colorless oil.

Step III: Preparation of Compound 14

To a solution of (3,5-Difluoro-4-((2-(trifluoromethyl) pyridin-4-yl)oxy)phenyl)methanol 14c (40 mg, 0.14 mmol) in dry N,N-dimethylformamide (5 mL) was added sodium hydride (60% in mineral oil, 11 mg, 0.28 mmol) at 0° C., and stirred at room temperature for 5 min. Then compound 1f (30 mg, 0.14 mmol) was added, and stirred for 1 h, quenched with a small amount of water. Purification via silica gel column chromatography with an eluent system (dichloromethane/methanol=10/1) afforded the title compound 14 (16 mg, 24.7%) as a white solid.

$^1$H NMR (400 MHz, $CDCl_3$) δ7.23 (m, m 1H), 7.13-7.05 (m, 2H), 6.80 (m, 1H), 6.70 (m, 1H), 5.43 (s, 2H), 4.33-4.25 (m, 2H), 4.20 (m, 2H), 3.77 (m, 2H), 3.46-3.36 (m, 2H), 2.32 (s, 3H). MS (ESI): m/z 461.9 $[M+H]^+$.

Example 15 Preparation of Compound 15

15

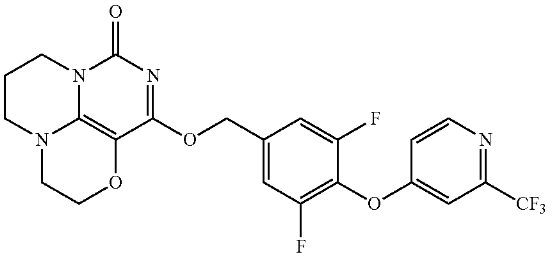

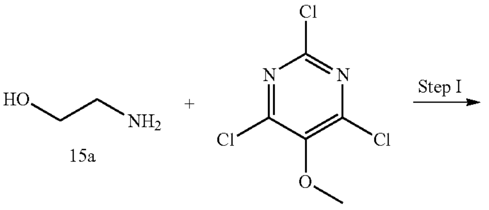

15a

1b

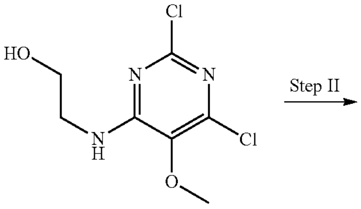

15b

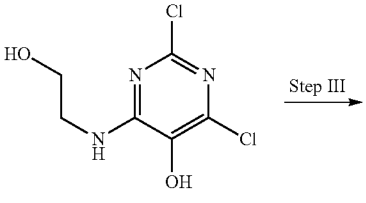

15c

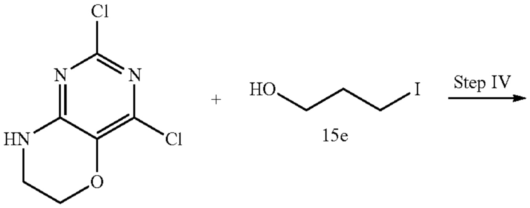

15e

15d

-continued

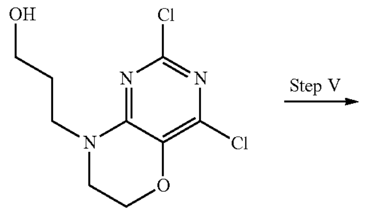

15f

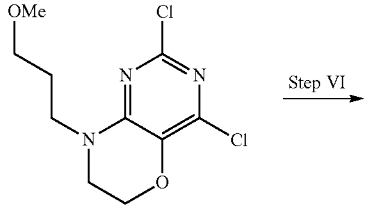

15g

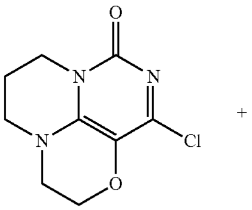

15h

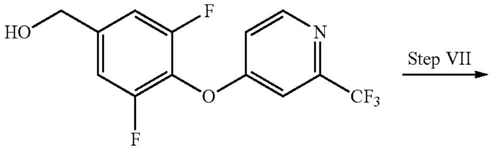

4d

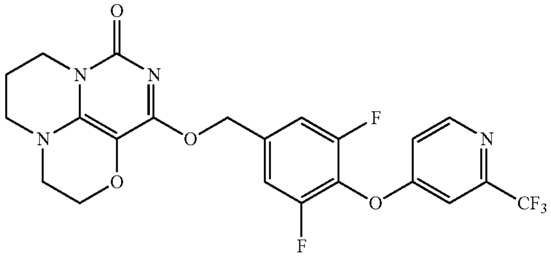

15

Step I: Preparation of Compound 15b

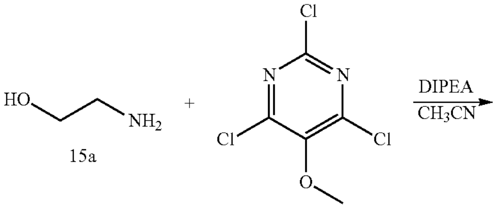

15a

1b

-continued

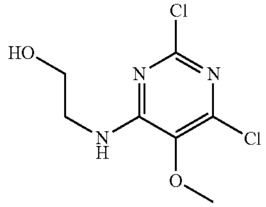

15b

At room temperature, 2,4,6-trichloro-5-methoxypyrimidine 1b (1.5 g, 7.03 mmol), ethanolamine 15a (0.64 g, 10.48 mmol) and diisopropylethylamine (1.36 g, 10.54 mmol) were dissolved in acetonitrile (70 mL), stirred and reacted for 3 h, concentrated under reduced pressure. Purification via silica gel column chromatography with an eluent system (dichloromethane/methanol=20/1) afforded the title compound 15b (1.35 g, Yield: 80.6%) as an oil.

$^1$H NMR (400 MHz, DMSO) δ7.99 (m, 1H), 4.77 (m, 1H), 3.73 (s, 3H), 3.52 (m, 2H), 3.39 (m, 2H).

Step II: Preparation of Compound 15c

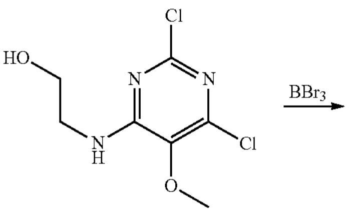

15b

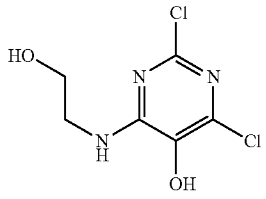

15c

Under the protection of argon, 15b (1.35 g, 5.7 mmol) was dissolved in anhydrous dichloromethane (50 mL), then boron tribromide (28.5 mL, 1M) was slowly added dropwise, and the reaction was stirred at 0° C. for 4 h. The reaction was quenched by adding methanol, concentrated under reduced pressure. Purification via silica gel column chromatography with an eluent system (dichloromethane/methanol=10/1) afforded the title compound 15c (1.09 g, Yield: 85.4%) as a white solid.

Step III: Preparation of Compound 15d

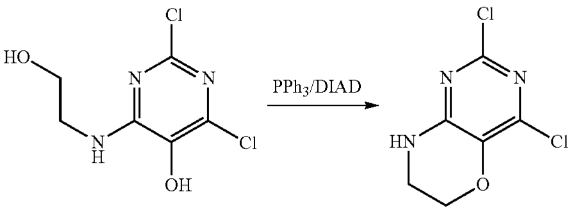

15c

15d

Under the protection of nitrogen, triphenylphosphine (3.8 g, 14.5 mmol) was dissolved in anhydrous THF (50 mL), then DIAD (2.87 mL, 14.6 mmol) was slowly added dropwise. The reaction mixture was stirred at 0° C. for 15 min, and 15c was added dropwise (1.09 g, 4.87 mmol) in THF/DMF solution (30 mL/5 mL), then stirred at 0° C. for 4 h, quenched by addition of water dropwise, extracted with ethyl acetate. The combined organic layers were dried over anhydrous sodium sulfate, concentrated under reduced pressure. Purification via silica gel column chromatography with an eluent system (dichloromethane/methanol=40/1) afforded the title compound 15d (1.0 g, Yield: 99.6%) as a white solid.

$^1$H NMR (400 MHz, $CDCl_3$) δ7.14 (s, 1H), 4.30 (m, 2H), 3.75-3.66 (m, 2H).

Step IV: Preparation of Compound 15f

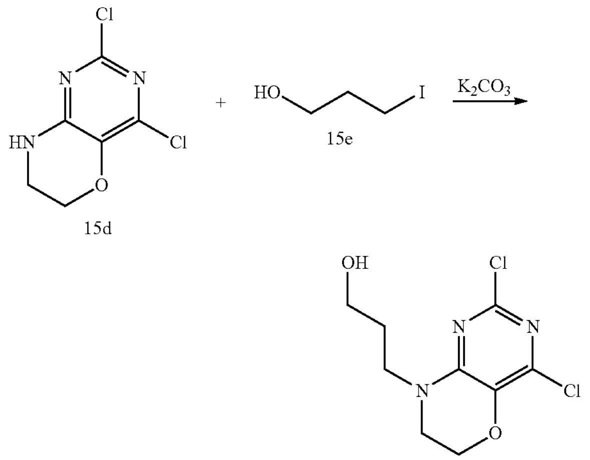

15d 15e 15f

At room temperature, 15d (1.0 g, 4.85 mmol) was dissolved in DMF (40 mL), followed by addition of potassium carbonate (0.92 g, 6.64 mmol) and 3-iodopropanol (1.23 g, 6.61 mmol). The reaction mixture was stirred at 80° C. for 2 h, quenched by addition of water the reaction, extracted with ethyl acetate. The combined organic layers were dried over anhydrous sodium sulfate, concentrated under reduced pressure. Purification via silica gel column chromatography with an eluent system (dichloromethane/methanol=20/1) afforded the title compound 15f (0.58 g, Yield: 45.3%) as a white solid.

$^1$H NMR (400 MHz, $CDCl_3$) δ4.26 (m, 2H), 3.77-3.70 (m, 2H), 3.61-3.54 (m, 3H), 3.30 (m, 1H), 1.84 (m, 2H).

Steps V and VI: Preparation of Compound 15h

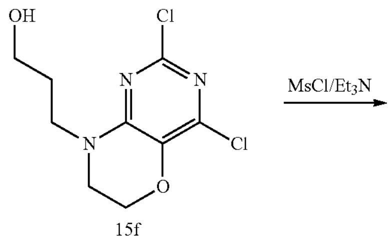

15f

-continued

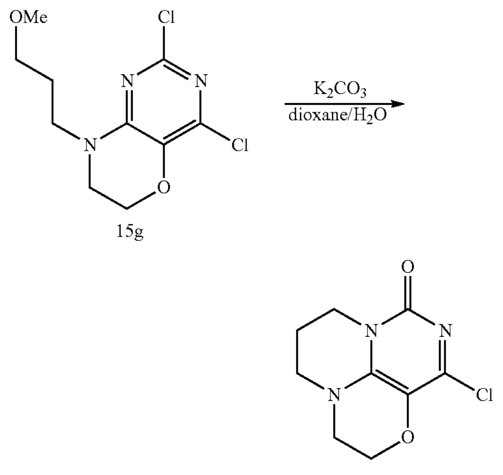

15g 15h

At room temperature, 15f (0.58 g, 2.2 mmol) and triethylamine (0.67 g, 6.6 mmol) were dissolved in dry dichloromethane (30 mL), then methanesulfonyl chloride (0.30 g, 2.6 mmol) was added dropwise at 0° C. The reaction mixture was stirred at 0° C. for 1 h, concentrated under reduced pressure. The crude product from the previous step was dissolved in mixed solvent of dioxane/water (60 mL, 1/1), followed by addition of potassium carbonate (0.9 g, 6.6 mmol) at room temperature. The reaction mixture was stirred at 90° C. overnight, concentrated under reduced pressure. Purification via silica gel column chromatography with an eluent system (dichloromethane/methanol=10/1) afforded the title compound 15h (85 mg, Yield: 16.8%) as a white solid.

$^1$H NMR (400 MHz, $CDCl_3$) δ4.19-4.14 (m, 2H), 3.97-3.90 (m, 2H), 3.56 (m, 2H), 3.44 (m, 2H), 2.14 (m, 2H).

Step VII: Preparation of Compound 15

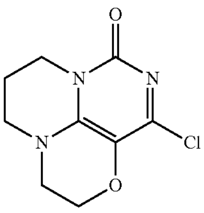

15h

+

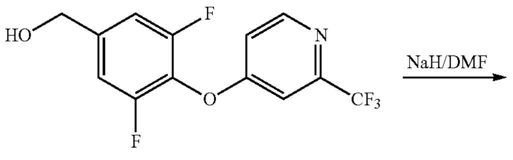

4d

-continued

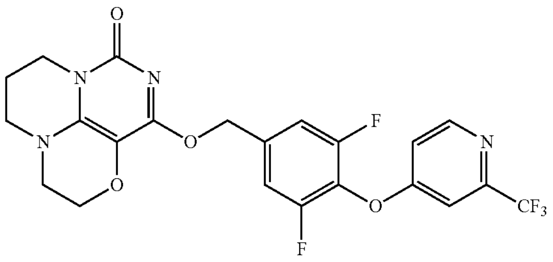

15

-continued

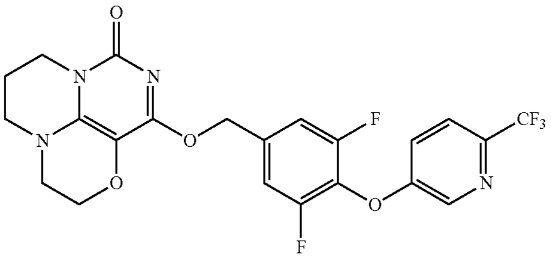

16

To a solution of (3,5-Difluoro-44(2-(trifluoromethyl)pyridin-4-yl)oxy)phenyl)methanol 4d (79 mg, 0.26 mmol) in dry N,N-dimethylformamide (5 mL) was added sodium hydride (60% in mineral oil, 11 mg, 0.28 mmol) at 0° C., and stirred at room temperature for 5 min. Then compound 15h (40 mg, 0.18 mmol) was added, and stirred for 1 h, quenched with a small amount of water. Purification via silica gel column chromatography with an eluent system (dichloromethane/methanol=10/1) afforded the title compound 15 (12 mg, 13.4%) as a white solid.

$^1$H NMR (400 MHz, $CDCl_3$) δ8.61 (m, 1H), 7.20 (m, 3H), 6.99 (m, 1H), 5.47 (m, 2H), 4.19 (m, 2H), 4.05-3.97 (m, 2H), 3.58-3.50 (m, 2H), 3.40 (m, 2H), 2.17 (m, 2H). MS (ESI): m/z 497.1 $[M+H]^+$.

Example 16 Preparation of Compound 16

16

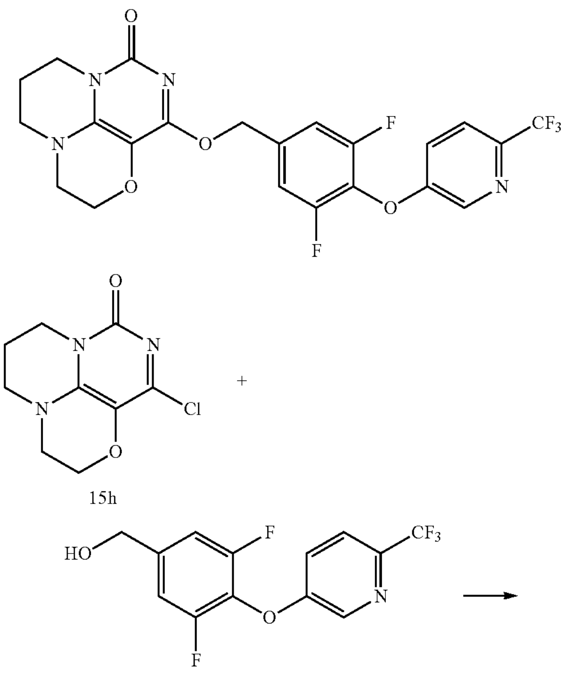

15h

5c

To a solution of (3,5-Difluoro-44(6-(trifluoromethyl)pyridin-3-yl)oxy)phenyl)methanol 5c (61 mg, 0.2 mmol) in dry N,N-dimethylformamide (5 mL) was added sodium hydride (60% in mineral oil, 8 mg, 0.2 mmol) at 0° C., and stirred at room temperature for 5 min. Then compound 15h (30 mg, 0.13 mmol) was added, and stirred for 1 h, quenched with a small amount of water. Purification via silica gel column chromatography with an eluent system (dichloromethane/methanol=10/1) afforded the title compound 16 (11 mg, 17.0%) as a white solid.

$^1$H NMR (400 MHz, $CDCl_3$) δ8.49 (m, 1H), 7.62 (m, 1H), 7.28 (m, m 1H), 7.17 (m, 2H), 5.43 (s, 2H), 4.17 (m, 2H), 4.03-3.95 (m, 2H), 3.55-3.49 (m, 2H), 3.37 (m, 2H), 2.15 (m, 2H). MS (ESI): m/z 497.1 $[M+H]^+$.

Example 17 Preparation of Compound 17

17

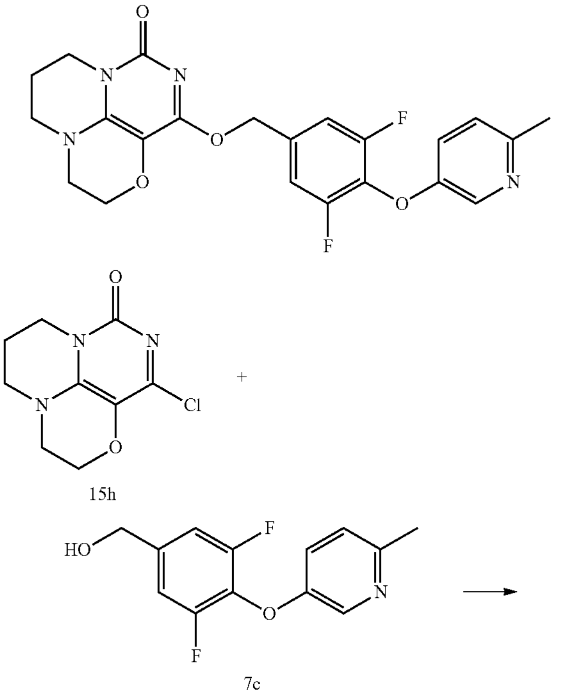

15h

7c

-continued

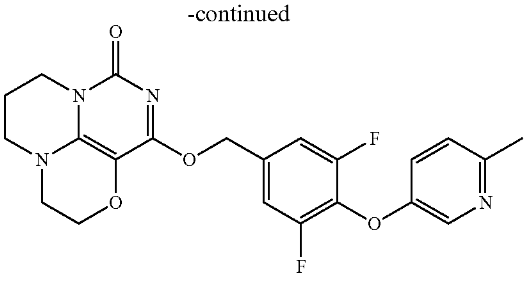

17

To a solution of (3,5-Difluoro-4-((6-methylpyridin-3-yl)oxy)phenyl)methanol 7c (50 mg, 0.2 mmol) in dry N,N-dimethylformamide (5 mL) was added sodium hydride (60% in mineral oil, 8 mg, 0.2 mmol) at 0° C., and stirred at room temperature for 5 min. Then compound 15h (30 mg, 0.13 mmol) was added, and stirred for 1 h, quenched with a small amount of water. Purification via silica gel column chromatography with an eluent system (dichloromethane/methanol=10/1) afforded the title compound 17 (18 mg, 31.3%) as a white solid.

$^1$H NMR (400 MHz, $CDCl_3$) δ8.26 (s, 1H), 7.09 (m, 4H), 5.42 (s, 2H), 4.16 (m, 2H), 3.99 (m, 2H), 3.51 (m, 2H), 3.36 (m, 2H), 2.51 (s, 3H), 2.14 (m, 2H). MS (ESI): m/z 443.1 $[M+H]^+$.

Example 18 Preparation of Compound 18

18

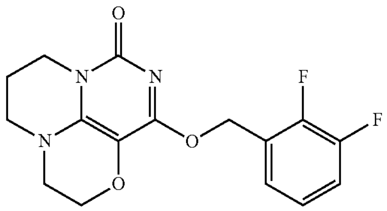

To a solution of (2,3-Difluorophenyl)methanol (38 mg, 0.26 mmol) in dry N,N-dimethylformamide (5 mL) was added sodium hydride (60% in mineral oil, 11 mg, 0.28 mmol) at 0° C., and stirred at room temperature for 5 min. Then compound 15h (40 mg, 0.18 mmol) was added, and stirred for 1 h, quenched with a small amount of water. Purification via silica gel column chromatography with an eluent system (dichloromethane/methanol=10/1) afforded the title compound 18 (16 mg, 26.5%) as a white solid.

$^1$H NMR (400 MHz, $CDCl_3$) δ7.45 (m, 1H), 6.95-6.83 (m, 2H), 5.42 (s, 2H), 4.20 (m, 2H), 4.04-3.95 (m, 2H), 3.56-3.49 (m, 2H), 3.40 (m, 2H), 2.16 (m, 2H). MS (ESI): m/z 336.1 $[M+H]^+$.

Example 19 Preparation of Compound 19

19

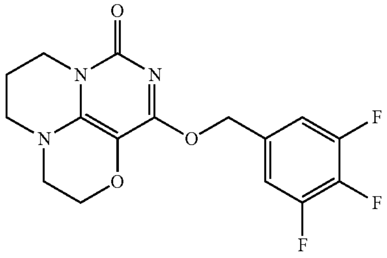

To a solution of (3,4,5-Trifluorophenyl)methanol (42 mg, 0.26 mmol) in dry N,N-dimethylformamide (5 mL) was added sodium hydride (60% in mineral oil, 11 mg, 0.28 mmol) at 0° C., and stirred at room temperature for 5 min. Then compound 15h (40 mg, 0.18 mmol) was added, and stirred for 1 h, quenched with a small amount of water. Purification via silica gel column chromatography with an eluent system (dichloromethane/methanol=10/1) afforded the title compound 19 (15 mg, 23.6%) as a white solid.

$^1$H NMR (400 MHz, $CDCl_3$) δ7.33 (m, 2H), 5.43 (s, 2H), 4.20 (m, 2H), 4.06-3.96 (m, 2H), 3.57-3.49 (m, 2H), 3.41 (m, 2H), 2.18 (m, 2H). MS (ESI): m/z 354.1 $[M+H]^+$.

Biological Evaluation

The biological activity of the compounds can be determined by using any suitable assay and tissue and in vivo models for determining the activity of the compounds as LpPLA2 inhibitors.

(1) Recombinant Human Lp-PLA2 (rhLp-PLA2) Assay (Also Known as PED6 Assay)

PED6 is a fluorescently labeled phospholipid that can be purchased directly from Invitogene or Molecular Probes. There is a fluorescence-quenching p-nitrophenyl group on the Sn3 position, and a Bodipy fluorescein (FL) group on the sn2 position. Once it is cleaved by the Lp-PLA2 enzyme, the FL group is released, resulting in enhanced fluorescence. However, Lp-PLA2 inhibitors can prevent this cleavage, so that no fluorescence enhancement is observed Assay method: The compound to be tested (as shown in Table 1) was mixed with DMSO solution at a volume ratio of 1:3, diluted to prepare a source plate of a 384-well microplate. Then 0.01 μl of the compound was transferred via an ECHO liquid dispenser from the source plate to a 384-well Greiner 784076 plate, and 5 microliters of a buffer composed of 50 mM HEPES, pH7.4, 150 mM NaCl, 1 mM CHAPS (the buffer solution contains Recombinant human Lp-PLA2 enzyme at a concentration of 4 nM or 110 pM) was added to each well on the plate. The plate was centrifuged at 500 rpm for 10 seconds. After 30 minutes of pre-incubation, 5 microliters of the above buffer solution was added to a 384-well Greiner784076 plate, and the plate was centrifuged at 500 rpm for 10 seconds. After the plate was incubated at room temperature for 20 min in the dark, the fluorescence intensity was read at ex 480/em 540 with a ViewLux microplate imager, and the Excel's XL fitting model was used to performe curve and QC analysis to calculate pIC50. The results are listed in Table 1.

TABLE 1

| Compound No. | rhLp-PLA2 ($pIC_{50}$) |
|---|---|
| 1 | 7.8 |
| 2 | 8.0 |
| 3 | 8.5 |
| 4 | 9.9 |
| 5 | 9.7 |
| 6 | 9.8 |
| 7 | 9.6 |
| 8 | 9.0 |
| 9 | 9.8 |
| 10 | 9.7 |
| 11 | 10.0 |
| 12 | 10.1 |
| 13 | 9.8 |
| 14 | 9.7 |
| 15 | 10.2 |
| 16 | 10.1 |
| 17 | 10.3 |
| 18 | 8.0 |
| 19 | 8.4 |
| Positive Compound Rilapladib | 8.9 |

(2) Human Plasma Lp-PLA2 Assay (Also Known as Thio-PAF Assay)

The human plasma assay was conducted using the sulphatide analog of PAF (phosphatidylcholine), which is hydrolyzed to produce phospholipids containing free sulfhydryl groups, subjected to Michael addition with CPM to generate fluorescence-enhancing maleimide.

Continuous quantitative analysis of thiol could be conducted by detecting the fluorescence intensity.

This assay can be used to detect the inhibitory activity of the Lp-PLA2 inhibitor on the Lp-PLA2 enzyme in human plasma.

Assay Method: The compound to be tested (as shown in Table 2) was mixed with a DMSO solution in a volume ratio of (1:3), and diluted to prepare a source plate of a 384-well microplate. Then 0.01 µl of the compound was transferred via an ECHO liquid dispenser from the source plate to a 384-well Greiner 784076 low-volume plate, and 8 µl of pre-aliquoted and frozen mixed human plasma was added. The plate was centrifuged at 500 rpm for 10 seconds. After a 30 min pre-incubation, 2 µl of a substrate solution, and containing 2.5 mM 2-thio-PAF (a solution in ethanol), 32 µM CPM (a solution in DMSO) and a buffer of 3.2 mM N-ethylmaleimide (NEM) (a buffer solution consisting of 50 mM HEPES, pH7.4, 150 mM NaCl, 1 mM CHAPS) was added by a BRAVO liquid handling station to a 384-well Greiner 784076 low-volume plate. After 2 min, the reaction was quenched with 5 µl of 5% trifluoroacetic acid. After the plate was incubated at room temperature for 40 min in a dark place, the fluorescence intensity was read at ex 380/em 485 with an Envision microplate reader, and the XL fitting model in Excel was used to perform the curve analysis and QC analysis to calculate pIC50. The results are shown in Table 2.

TABLE 2

| Compound No. | Thio-PAF ($pIC_{50}$) |
|---|---|
| 1 | 6.5 |
| 2 | 6.8 |
| 3 | 7.3 |
| 4 | 7.9 |
| 5 | 7.7 |
| 6 | 7.8 |
| 7 | 7.7 |
| 8 | 7.4 |
| 9 | 8.0 |
| 10 | 7.8 |
| 11 | 8.0 |
| 12 | 7.8 |
| 13 | 7.9 |
| 14 | 7.8 |
| 15 | 8.1 |
| 16 | 8.0 |
| 17 | 8.1 |
| 18 | 6.9 |
| 19 | 7.2 |
| Positive compound Rilapladib | 7.8 |

What is claimed is:

1. A compound of Formula (I) or a pharmaceutically acceptable salt thereof, (I)

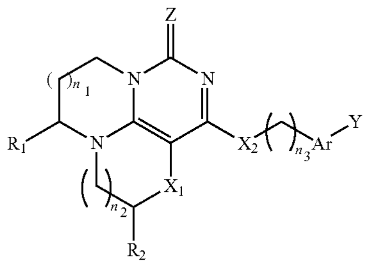

wherein $n_1$ is 0 or 1, $n_2$ and $n_3$ are each independently 1;

$R_1$ and $R_2$ are each independently selected from the group consisting of H, hydroxyl, cyano, halogen, alkyl, deuterated alkyl, hydroxyalkyl, haloalkyl, cycloalkyl, alkoxy, haloalkoxy, or deuterated alkoxy;

$X_1$ and $X_2$ are each independently selected from the group consisting of O or S;

Ar is an arylene group or a heteroarylene group wherein hydrogen atoms in the arylene group or the heteroarylene group are optionally substituted by 0, 1 or more substituents, and the substituents are each independently selected from the group consisting of halogen, alkyl, deuteroalkyl, haloalkyl, alkoxy, deuteroalkoxy, haloalkoxy, or cycloalkyl;

Y is selected from the group consisting of H, halogen, alkyl, haloalkyl, haloalkoxy, cycloalkyl, alkoxy, deuterated alkyl, deuterated alkoxy, —OAr', or —SAr';

Ar' is aryl or heteroaryl, wherein hydrogen atoms in the aryl or heteroaryl are optionally substituted with one or more substituents, the substituents are each independently selected from the group consisting of halogen, alkyl, deuterated alkyl, haloalkyl, alkoxy, deuterated alkoxy, hydroxyalkyl, haloalkoxy, cyano, or cycloalkyl;

Z is O or S;

wherein, the halogens in the "halogen" "haloalkyl" and "haloalkoxy" are each independently selected from the group consisting of F, Cl, Br, or I;

the alkyls in the "alkyl" "deuterated alkyl" "hydroxyalkyl" "haloalkyl" "haloalkoxy", and "alkoxy" are each independently $C_1$-$C_{10}$ linear or branched alkyl;

the cycloalkyl is $C_5$-$C_{10}$ monocyclic or bicyclic cycloalkyl;

the aryl is 6- to 10-membered aryl; the arylene is 6- to 10-membered arylene;

the heteroaryl is 5- to 10-membered heteroaryl ring containing 1-3 heteroatoms selected from the group consisting of N, O, or S.

2. The compound or a salt thereof according to claim 1, wherein "alkyls" in the "alkyl" "deuterated alkyl" "hydroxyalkyl" "haloalkyl" "haloalkoxy", and "alkoxy" are each independently $C_1$-$C_7$ linear or branched alkyl;

"cycloalkyl" is $C_3$-$C_7$ monocyclic cycloalkyl;

"aryl" is phenyl or naphthyl;

"arylene" is phenylene or naphthylene;

"heteroaryl" is 5- to 10-membered heteroaryl ring containing 1-2 heteroatoms selected from N, O, and S.

3. The compound or a salt thereof according to claim 1, wherein $R_1$ and $R_2$ are each independently selected from the group consisting of H, fluorine, chlorine, bromine, hydroxyl, cyano, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, 2,2,3-trimethylbutyl, $—CD_3$, $—C_2D_5$, $—C_3D_7$, $—OCD_3$, $—OC_2D_5$, $—OC_3D_7$, haloalkyl, haloalkoxyl, cyclopropanyl, cyclobutanyl, or cyclopentanyl;

Ar is phenylene or pyridyl, wherein hydrogen atoms in the phenylene or pyridyl are optionally substituted with 0, 1, 2, or 3 substituents, the substituents are each independently selected from the group consisting of F, Cl, Br, I, -Me, $—C_2H_5$, cyclopropyl, $—CD_3$, —OMe, $—OCD_3$, $—CF_3$, or $—OCF_3$;

Y is selected from the group consisting of —H, —F, —Cl, —Br, methyl, ethyl, n-propyl, isopropyl, $—CD_3$, $—CF_3$, $—CH_2CF_3$, $—OCF_3$, $—OCHF_2$, $—OCH_2F$, cyclopropyl, cyclobutyl, cyclopentyl, $—OCH_3$, $—OCD_3$, $—OC_2H_5$, $—OCH_7$, or —OAr';

Ar' is selected from the group consisting of phenyl, pyridyl, pyrimidyl, pyrrolyl, pyrazolyl, thienyl or quinolinyl, wherein hydrogen atoms in the phenyl, pyridyl, pyrimidyl, pyrrolyl, pyrazolyl, thienyl or quinolinyl ring are each independently optionally substituted with 1, 2, or 3 substituents, the substituents are each independently selected from the group consisting of F, Cl, Br, —CN, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, 2,2,3-trimethylbutyl, $—CD_3$, $C_1$-$C_6$ haloalkyl, $—OCH_3$, $—OCD_3$, $—OC_2H_5$, $—OCH_7$, $C_1$-$C_6$ haloalkoxyl, or $C_5$-$C_6$ cycloalkyl;

Z is O.

4. The compound of Formula (I) or a pharmaceutically acceptable salt thereof according to claim 1, wherein the compound of Formula (I) is selected from the following compounds:

1

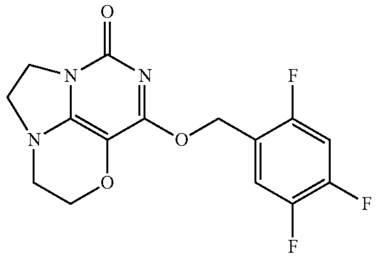

2

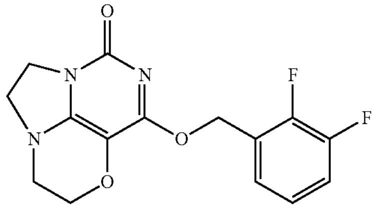

3

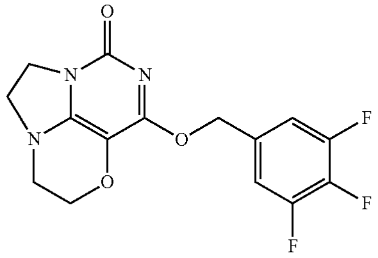

4

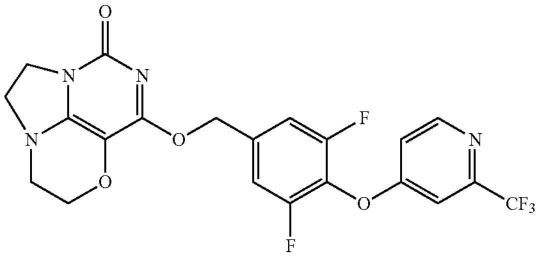

5

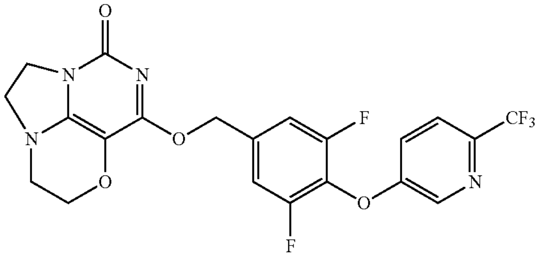

-continued
6
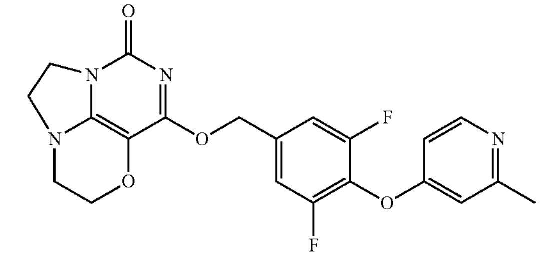
7
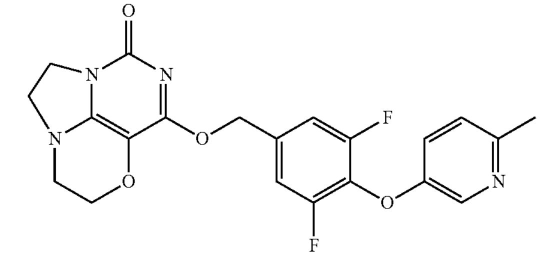
8
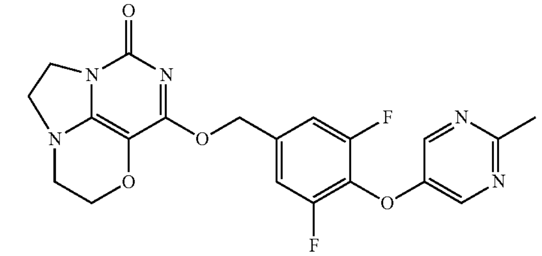
9
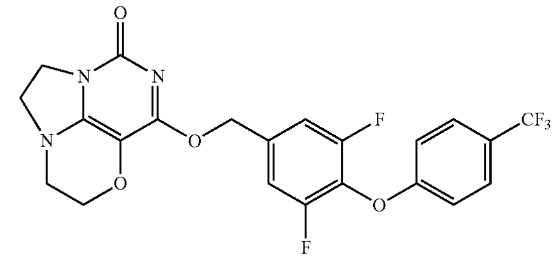
10
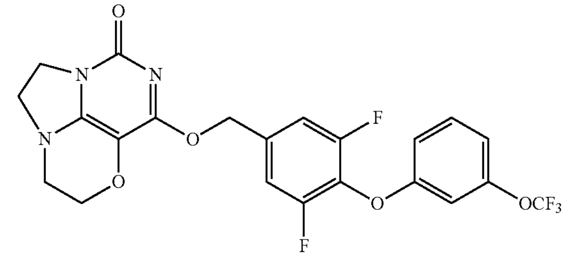
11
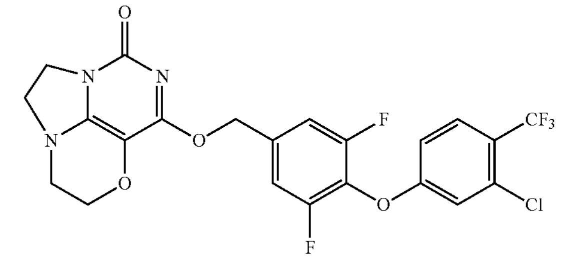
-continued
12
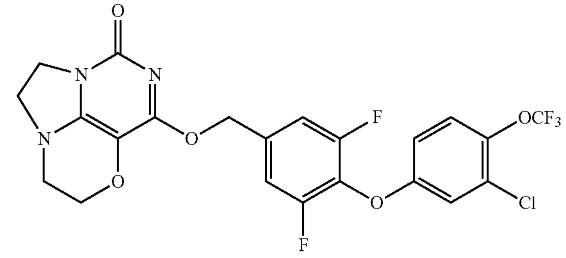
13
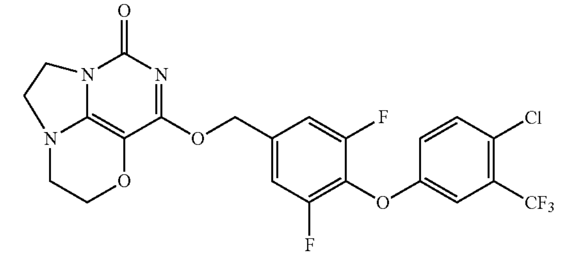
14
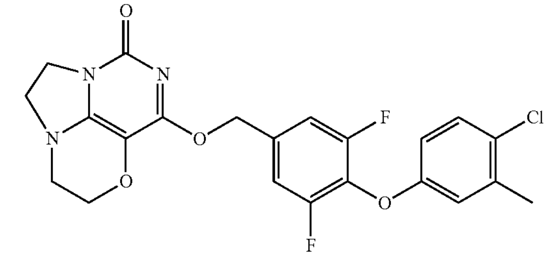
15
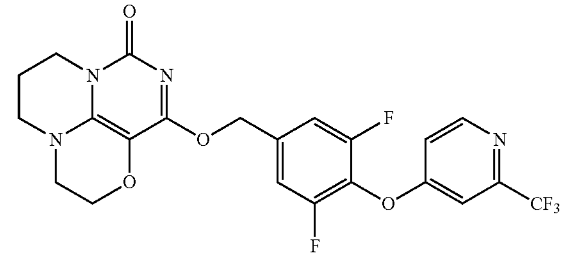
16
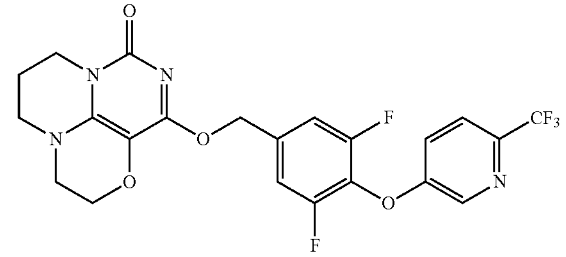

-continued

17

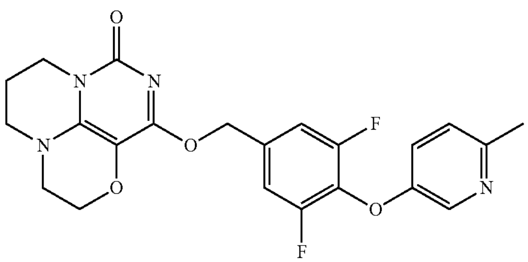

18

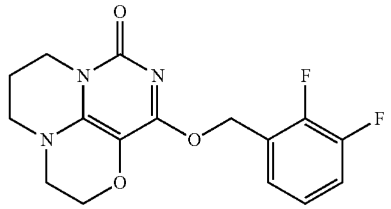

19

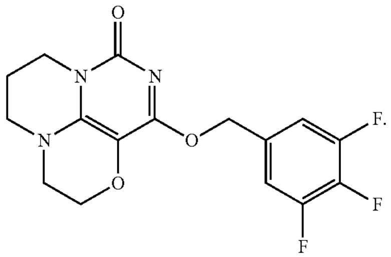

5. The compound of Formula (I) or a pharmaceutically acceptable salt thereof according to claim 1, wherein the pharmaceutically acceptable salt is an anionic salt or cationic salt of the compound of Formula (I).

6. A preparation method of the compound of Formula (I) or a pharmaceutically acceptable salt thereof according to claim 1, comprising the step of reacting a compound of Formula (II) with a compound of Formula (III) to produce the compound of Formula (I):

(II)

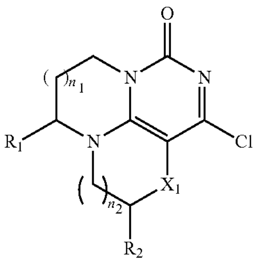

(III)

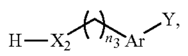

wherein $n_1$ is 0 or 1;

$n_2$ and $n_3$ are each independently 1;

$R_1$ and $R_2$ are each independently selected from the group consisting of H, hydroxyl, cyano, halogen, alkyl, deuterated alkyl, hydroxyalkyl, haloalkyl, cycloalkyl, alkoxy, haloalkoxy, or deuterated alkoxy;

$X_1$ and $X_2$ are each independently selected from the group consisting of O or S;

Ar is an arylene group or a heteroarylene group wherein hydrogen atoms in the arylene group or the heteroarylene group are optionally substituted by 0, 1 or more substituents, and the substituents are each independently selected from the group consisting of halogen, alkyl, deuteroalkyl, haloalkyl, alkoxy, deuteroalkoxy, haloalkoxy, or cycloalkyl;

Y is selected from the group consisting of H, halogen, alkyl, haloalkyl, haloalkoxy, cycloalkyl, alkoxy, deuterated alkyl, deuterated alkoxy, —OAr', or —SAr';

Ar' is aryl or heteroaryl, wherein hydrogen atoms in the aryl or heteroaryl are optionally substituted with one or more substituents, the substituents are each independently selected from the group consisting of halogen, alkyl, deuterated alkyl, haloalkyl, alkoxy, deuterated alkoxy, hydroxyalkyl, haloalkoxy, cyano, or cycloalkyl;

wherein, the halogens in the "halogen" "haloalkyl" and "haloalkoxy" are each independently selected from the group consisting of F, Cl, Br, or I;

the alkyls in the "alkyl" "deuterated alkyl" "hydroxyalkyl" "haloalkyl" "haloalkoxy", and "alkoxy" are each independently $C_1$-$C_{10}$ linear or branched alkyl;

the cycloalkyl is $C_5$-$C_{10}$ monocyclic or bicyclic cycloalkyl;

the aryl is 6- to 10-membered aryl; the arylene is 6- to 10-membered arylene;

the heteroaryl is 5- to 10-membered heteroaryl ring containing 1-3 heteroatoms selected from the group consisting of N, O, or S.

7. A pharmaceutical composition, comprising a therapeutically effective amount of one or more of the compound of Formula (I) or a pharmaceutically acceptable salt thereof according to claim 1, and optionally, pharmaceutically acceptable excipient(s).

8. The pharmaceutical composition according to claim 7, wherein the dosage form of the pharmaceutical composition is oral, rectal, or parenteral formulation.

9. A method of treating Alzheimer's disease, glaucoma, or age-related macular degeneration in a subject in need thereof, comprising administering to the subject a compound of Formula (I) or a pharmaceutically acceptable salt thereof according to claim 1.

10. A method of treating atherosclerosis, diabetic macular edema, or prostate cancer in a subject in need thereof, comprising administering to the subject a compound of Formula (I) or a pharmaceutically acceptable salt thereof according to claim 1.

11. The compound of Formula (I) or a pharmaceutically acceptable salt thereof according to claim 1, wherein the pharmaceutically acceptable salt is a salt formed by the compound of Formula (I) and an organic base, and wherein the organic base is selected from the group consisting of trialkylamine, pyridine, quinoline, piperidine, imidazole, picoline, dimethylaminopyridine, dimethylaniline, N-alkylmorpholine, 1,5-diazabicyclo[4.3.0]nonene-5,1,8-diazabicyclo[5.4.0]undecene-7,1,4-diazabicyclo[2.2.2]octane, and combinations thereof;

or the pharmaceutically acceptable salt is a salt formed by the compound of Formula (I) and an acid, wherein the acid is selected from the group consisting of hydrochloric acid, hydrobromic acid, hydroiodic acid, sulfuric acid, nitric acid, phosphoric acid, carbonic acid, formic acid, acetic acid, propionic acid, oxalic acid, malonic acid, succinic acid, fumaric acid, maleic acid, lactic acid, malic acid, citric acid, tartaric acid, picric acid, methanesulfonic acid, ethanesulfonic acid, p-toluenesulfonic acid, glutamic acid, pamoic acid, and combinations thereof.

12. A preparation method of the compound of Formula (I) or a pharmaceutically acceptable salt thereof according to claim 1, comprising the following steps:

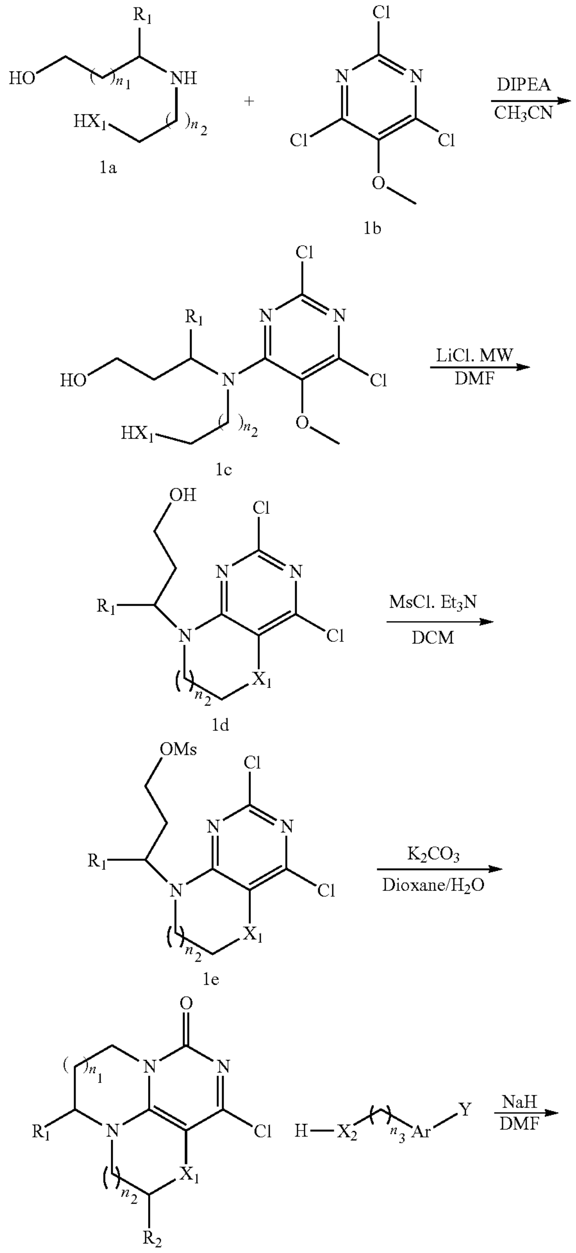

1a 1b 1c 1d 1e

-continued

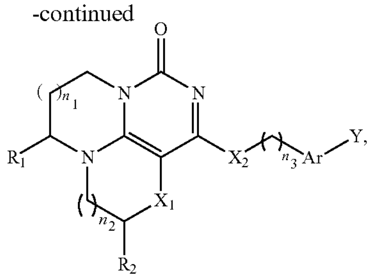

wherein $n_1$ is 0 or 1;

$n_2$ and $n_3$ are each independently 1;

$R_1$ and $R_2$ are each independently selected from the group consisting of H, hydroxyl, cyano, halogen, alkyl, deuterated alkyl, hydroxyalkyl, haloalkyl, cycloalkyl, alkoxy, haloalkoxy, or deuterated alkoxy;

$X_1$ and $X_2$ are each independently selected from the group consisting of O or S;

Ar is an arylene group or a heteroarylene group wherein hydrogen atoms in the arylene group or the heteroarylene group are optionally substituted by 0, 1 or more substituents, and the substituents are each independently selected from the group consisting of halogen, alkyl, deuteroalkyl, haloalkyl, alkoxy, deuteroalkoxy, haloalkoxy, or cycloalkyl;

Y is selected from the group consisting of H, halogen, alkyl, haloalkyl, haloalkoxy, cycloalkyl, alkoxy, deuterated alkyl, deuterated alkoxy, —OAr', or —SAr';

Ar' is aryl or heteroaryl, wherein hydrogen atoms in the aryl or heteroaryl are optionally substituted with one or more substituents, the substituents are each independently selected from the group consisting of halogen, alkyl, deuterated alkyl, haloalkyl, alkoxy, deuterated alkoxy, hydroxyalkyl, haloalkoxy, cyano, or cycloalkyl;

wherein, the halogens in the "halogen" "haloalkyl" and "haloalkoxy" are each independently selected from the group consisting of F, Cl, Br, or I;

the alkyls in the "alkyl" "deuterated alkyl" "hydroxyalkyl" "haloalkyl" "haloalkoxy", and "alkoxy" are each independently $C_1$-$C_{10}$ linear or branched alkyl;

the cycloalkyl is $C_5$-$C_{10}$ monocyclic or bicyclic cycloalkyl;

the aryl is 6- to 10-membered aryl; the arylene is 6- to 10-membered arylene;

the heteroaryl is 5- to 10-membered heteroaryl ring containing 1-3 heteroatoms selected from the group consisting of N, O, or S.

13. The pharmaceutical composition according to claim 8, wherein the dosage form is selected from the group consisting of solid, liquid formulation, tablet, powder, granule, capsule, aqueous, oily suspension, syrup, solution for injection, aqueous, or oily suspension.

* * * * *